United States Patent [19]
Lenk et al.

[11] Patent Number: 5,925,375
[45] Date of Patent: Jul. 20, 1999

[54] THERAPEUTIC USE OF MULTILAMELLAR LIPOSOMAL PROSTAGLANDIN FORMULATIONS

[75] Inventors: Robert P. Lenk, The Woodland, Tex.; Michelle L. Tomsho, Levittown, Pa.; Robert L. Suddith, Wilmington, N.C.; Robert J. Klimchak, Flemington, N.J.; Andrew S. Janoff, Yardley, Pa.; Sharma R. Minchey, Monmouth Junction; Marc J. Ostro, Pennington, both of N.J.

[73] Assignee: The Liposome Company, Inc., Princeton, N.J.

[21] Appl. No.: 08/333,770

[22] Filed: Nov. 3, 1994

Related U.S. Application Data

[63] Continuation-in-part of application No. 08/152,852, Nov. 16, 1993, abandoned, which is a continuation-in-part of application No. 07/821,648, Jan. 16, 1992, Pat. No. 5,262,168, which is a continuation of application No. 07/195,228, May 18, 1988, Pat. No. 5,082,664, which is a continuation-in-part of application No. 07/053,305, May 2, 1987, abandoned, said application No. 08/152,852, is a continuation-in-part of application No. 08/147,898, Nov. 4, 1993, abandoned, which is a continuation of application No. 07/876,200, Apr. 30, 1992, abandoned, which is a continuation-in-part of application No. 07/697,314, May 7, 1991, abandoned.

[51] Int. Cl.$^6$ ............................ A61K 9/127; A61K 9/133
[52] U.S. Cl. ............................................. 424/450; 514/573
[58] Field of Search .............................. 424/450; 514/573

[56] References Cited

U.S. PATENT DOCUMENTS

| | | | |
|---|---|---|---|
| 3,993,754 | 11/1976 | Rahman et al. | 424/450 |
| 4,145,410 | 3/1979 | Sears | 424/450 |
| 4,224,179 | 9/1980 | Schneider | 252/316 |
| 4,229,360 | 10/1980 | Schneider et al. | 260/403 |
| 4,235,871 | 11/1980 | Papahadjopoulos et al. | 424/450 |
| 4,370,349 | 1/1983 | Evans et al. | 264/4.1 |
| 4,493,847 | 1/1985 | Mizushuma et al. | 424/317 |
| 4,522,803 | 6/1985 | Lenk et al. | 424/1.1 |
| 4,588,578 | 5/1986 | Fountain et al. | 424/1.1 |
| 4,684,633 | 8/1987 | Imagawa et al. | 514/78 |
| 4,820,732 | 4/1989 | Shell | 514/573 |
| 4,837,028 | 6/1989 | Allen et al. | 424/450 |
| 4,880,635 | 11/1989 | Janoff | 424/450 |

(List continued on next page.)

FOREIGN PATENT DOCUMENTS

| | | |
|---|---|---|
| 0097481 | 1/1984 | European Pat. Off. . |
| 0150732 | 8/1985 | European Pat. Off. . |
| 0 153 858 | 9/1985 | European Pat. Off. . |
| 0153858 | 9/1985 | European Pat. Off. . |
| 0 416 527 | 9/1990 | European Pat. Off. ....... A61K 9/127 |
| 0 512 916 | 11/1992 | European Pat. Off. ..... A61K 31/557 |
| 0 292 403 | 8/1994 | European Pat. Off. ..... A61K 31/557 |
| 61-100518 | 5/1986 | Japan . |
| 4-356421 | 12/1992 | Japan .......................... A61K 31/557 |
| 5-139977 | 6/1993 | Japan ............................ A61K 9/127 |
| 2050287 | 1/1981 | United Kingdom . |
| 85/00968 | 3/1985 | WIPO . |
| 85/04578 | 10/1985 | WIPO . |
| 86/00238 | 1/1986 | WIPO . |
| 86/01102 | 2/1986 | WIPO . |
| 86/01103 | 2/1986 | WIPO . |
| 87/00043 | 1/1987 | WIPO . |
| 88/09170 | 12/1988 | WIPO . |

*Primary Examiner*—Gollamudi S. Kishore
*Attorney, Agent, or Firm*—Kenneth Rubin; Rosanne Goodman

[57] ABSTRACT

This invention provides a multilamellar liposome containing an arachidonic acid metabolite, two or more lipid-containing bilayers and two or more aqueous compartments containing a release-inhibiting buffer. Preferred arachidonic acid metabolites are the prostaglandins, particularly $PGE_1$. The liposomal formulations can be used to treat animals, particularly humans, for diseases, disorders or conditions which can be ameliorated by prostaglandins, e.g., disorders characterized by cellular activation and adhesion, inflammation and/or toxemia.

19 Claims, 14 Drawing Sheets

U.S. PATENT DOCUMENTS

| | | | |
|---|---|---|---|
| 4,920,016 | 4/1990 | Allen et al. | 424/450 |
| 4,944,941 | 7/1990 | Ammann | 424/85.5 |
| 4,955,878 | 9/1990 | See et al. | 604/181 |
| 4,975,282 | 12/1990 | Cullis et al. | 424/450 |
| 5,008,050 | 4/1991 | Cullis et al. | 264/4.3 |
| 5,013,556 | 5/1991 | Woodle et al. | 424/450 |
| 5,030,453 | 7/1991 | Lenk et al. | 424/450 |
| 5,059,421 | 10/1991 | Loughrey et al. | 424/417 |
| 5,064,817 | 11/1991 | Yedger | 514/181 |
| 5,068,251 | 11/1991 | Brooks | 514/506 |
| 5,077,056 | 12/1991 | Bally et al. | 424/450 |
| 5,082,664 | 1/1992 | Lenk | 424/450 |
| 5,091,180 | 2/1992 | Walker | 514/568 |
| 5,169,637 | 12/1992 | Lenk et al. | 424/450 |
| 5,262,168 | 11/1993 | Leuk | 424/450 |

Release of PGE$_1$ from EPC or DPPC MLVs
*Incubated at RT at pH 7*

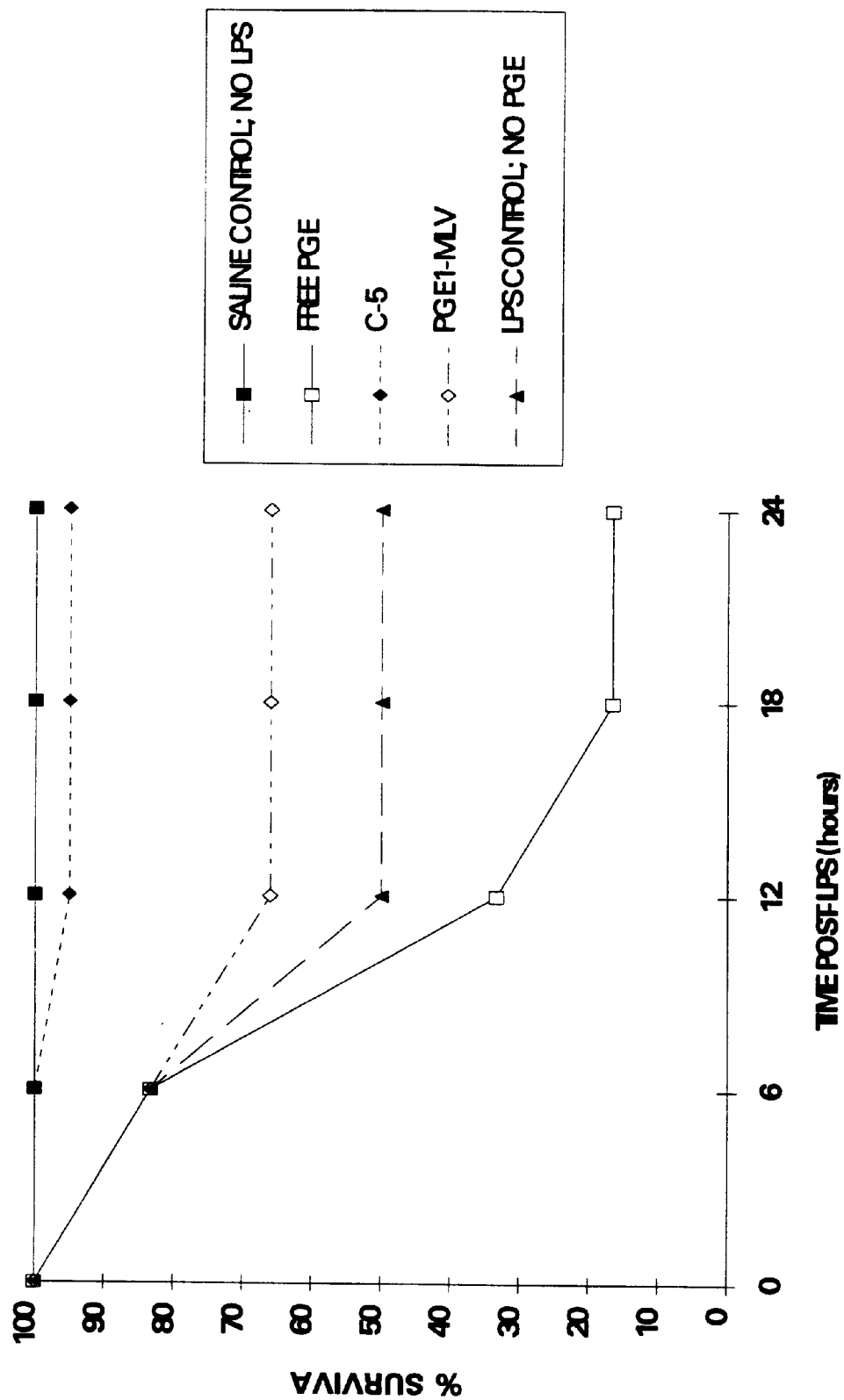

THERAPEUTIC USE OF MULTILAMELLAR LIPOSOMAL PROSTAGLANDIN FORMULATIONS

This application is a continuation-in-part of U.S. Ser. No. 08/152,852, filed Nov. 16, 1993, now abandoned which is a continuation-in-part of U.S. Ser. No. 07/821,648, filed Jan. 16, 1992, U.S. Pat. No. 5,262,168, which is a continuation of U.S. Ser. No. 07/195,228, filed May 18, 1988, now U.S. Pat. No. 5,082,664, which-in-turn is a continuation-in-part of U.S. Ser. No. 053,305, filed May 2, 1987, now abandoned, also U.S. Ser. No. 08/152,852 is also a continuation-in-part of U.S. Ser. No. 08/147,898, filed Nov. 4, 1993, now abandoned which is a continuation of U.S. Ser. No. 07/876,200, filed Apr. 30, 1992, now abandoned, which-in-turn is a continuation-in-part of U.S. Ser. No. 07/697,314, filed May 7, 1991 now abandoned, the contents of these patent applications are incorporated herein by reference.

This application is directed to multilamellar liposomal formulations of arachidonic acid metabolites; such formulations can be used therapeutically in diseases, disorders or conditions such as cell activation and adhesion disorders, inflammatory disorders or toxemic disorders.

Arachidonic acid, and other twenty carbon "essential" fatty acids having at least three double bonds, can be used to make prostaglandins (for a review, see, e.g., Goodman and Gilman's The Pharmacoloaical Basis of Therapeutics (A. Goodman Gilman et al., eds.), Pergamon Press, New York (1990), pp. 600–611); L. Stryer, Biochemistry (2nd edition), W. H. Freeman and Co,, New York (1981), pp. 853–854)). The various prostaglandins are grouped into several categories (A–I), which are distinguished by varying substituents on the five-carbon ring introduced into the twenty-carbon fatty acid precursor during prostaglandin synthesis. These groups can be further subdivided based upon the number, and position, of double bonds in the prostaglandins' carbon chains. Prostaglandins are believed to act on their target cells by way of cellular surface receptors; these receptors are believed to be coupled to second messenger systems by which prostaglandin action is mediated. Prostaglandins can have a broad spectrum of biological activities. They can act on smooth vascular muscle and thereby be potent vasodilators; prostaglandins can also affect the functioning of blood cells, particularly neutrophils and platelets. Uterine contractions can be affected by prostaglandin action, which can also affect renal, central nervous system and afferent nerve function, Various endocrine tissues can respond to prostaglandins. Furthermore, prostaglandins can modulate inflammatory conditions in animals.

Enzymes in the body can rapidly deactivate prostaglandins. This typically necessitates frequent administrations of high doses of the compounds to maintain therapeutically effective levels in the serum, thereby increasing the expense of prostaglandin treatment and leading to the possibility of unwanted side effects. Furthermore, as prostaglandin deactivation occurs primarily as blood passes through the lungs, the compounds are generally administered intra-arterially.

Liposomal formulations can prolong the circulatory half-lives of arachidonic acid metabolites, e.g., prostaglandins, and can help avoid their deactivation in the lungs. Accordingly, such liposomal formulations can useful provide therapeutic alternatives. Mizishuma et al. (J. Rheumatol. 14:97 (1987)) and Hoshi et al. (Drugs. Exptl. Clin. Res. 12(8):681 (1986)) describe lipid microspheres containing prostaglandin $E_1$ (PGE$_1$). However, as disclosed in Mizishuma et al. (U.S. Pat. No, 4,493,847) and Imagawa et al. (U.S. Pat. No. 4,684,633), these "microspheres" are actually prostaglandin-containing fat emulsions, which are not liposomes, and have neither the same properties, nor the same advantages, as the liposomal prostaglandins provided herein. Shell and See (U.S. Pat. Nos. 4,820,732 and 4,955,878) disclose treatments for reducing dysfunction during angioplasty procedures which involve administering prostaglandin-containing compositions to patients. These compositions also contain a carrier. However, the liquid carriers disclosed, e.g., dehydrated alcohols and saline solutions, generally cannot provide sustained release of a prostaglandin. The fat-laden microsphere carriers disclosed are taught to be at least as large as a red blood cell, i.e, at least 7microns in diameter, and can be much larger. Administration of particles of such large size to animals can cause difficulties because the microspheres can become stuck in, and clog, small blood vessels, e.g., lung capillaries.

Liposomes are self-assembling structures comprising one or more bilayers of amphipathic lipid molecules, each of which encloses an internal aqueous volume. Unilamellar liposomes have a single lipid bilayer. Multilamellar liposomes have two or more lipid bilayers. Liposomes can be produced by a variety of methods (for a review, see, e.g., Cullis et al., in: Liposomes, From Biophysics to Therapeutics (M. J. Ostro, ed.), Marcel Dekker, pp. 39–72 (1987), the contents of which are incorporated herein by reference).

Liposomal formulations of drugs can have an enhanced therapeutic index by reducing the drug's toxicity, increasing its efficacy, or both. Furthermore, liposomes, like other particulate matter in the circulation, are typically taken up by phagocytic cells of the reticuloendothelial system in tissues having sinusoidal capillaries, and are thereby often directed to sites of intracellular infections.

Maximizing the efficiency with which drugs are entrapped in liposomes can minimize the lipid load presented to treated subjects and can also minimize the waste of valuable drug products. The release of compounds which tend to leak from liposomes should also be inhibited to derive the maximum benefit from their encapsulation. Furthermore, the provision of liposomal formulations which can be stably stored will increase the therapeutic benefits derived therefrom.

The liposomal arachidonic acid metabolite formulations of this invention are useful in ameliorating or preventing diseases, disorders or conditions which can be treated with a prostaglandin. Disorders which can be treated with these formulations include cell activation and adhesion disorders, toxemic disorders and inflammatory disorders.

SUMMARY OF THE INVENTION

This invention provides a multilamellar liposome which comprises an arachidonic acid metabolite, two or more lipid bilayers comprising a lipid and two or more aqueous compartments comprising a release-inhibiting buffer.

Preferably, the multilamellar liposome comprises a solute entrapped in its aqueous compartments, wherein the concentration of the solute in each of the aqueous compartments of the multilamellar liposome is substantially equal; i.e., the multilamellar liposome of this invention preferably has substantially equal interlamellar solute distribution.

Preferably, the arachidonic acid metabolite is a prostaglandin. Preferred prostaglandins are prostaglandins of the E series or prostaglandins of the I series. Most preferably, the metabolite is prostaglandin E1 (PGE$_1$).

Preferably, the lipid has saturated acyl chains. In one embodiment of this invention, the saturated acyl chain lipid is dipalmitoyl phosphatidylcholine (DPPC). Preferably, the release-inhibiting buffer is a citric acid buffer, more preferably, a citric acid buffer having a pH of about 4.5.

The multilamellar liposome can comprise a drying protectant. Preferably, the drying protectant is a sugar, e.g., maltose, dextrose, galactose, lactose, raffinose or trehalose. Preferably, the sugar is maltose.

Accordingly, in a preferred embodiment of the invention, the multilamellar liposome comprises prostaglandin $E_1$, two or more lipid bilayers comprising DPPC and two or more aqueous compartments comprising a citric acid buffer having a pH of about 4.5. This preferred multilamellar liposome comprises a solute entrapped in its aqueous compartments, wherein the concentration of the solute in each of the aqueous compartments of the multilamellar liposome is substantially equal, and can comprise a drying protectant.

The multilamellar liposome of this invention can comprise an additional bioactive agent, i.e., a bioactive agent in addition to the arachidonic acid metabolite. The multilamellar liposome can further comprise a headgroup-modified lipid.

Also provided herein is a pharmaceutical composition comprising a pharmaceutically acceptable carrier and the multilamellar liposome of this invention. Further provided is a dehydrated multilamellar liposome comprising an arachidonic acid metabolite and two or more lipid bilayers comprising a lipid. Still further provided is a two-component system comprising an aqueous solution and such a dehydrated liposome, wherein the dehydrated multilamellar liposome and the aqueous solution are combined so as to rehydrate the dehydrated liposome.

This invention provides a method of administering an arachidonic acid metabolite to an animal which comprises administering to the animal a multilamellar liposome comprising the metabolite, two or more lipid bilayers comprising a lipid, and two or more compartments comprising an aqueous release-inhibiting aqueous buffer. Preferably, the administration comprises intravenous administration. Preferably, the animal is a human, Preferably, the arachidonic acid metabolite is prostaglandin E1. Preferably, the lipid is a saturated acyl chain lipid. Preferably the buffer is a citric acid buffer having a pH of about 4.5. The liposome preferably comprises a solute entrapped in its aqueous compartments, wherein the concentration of the solute in each of the compartments is substantially equal.

The animal can be afflicted with a disorder characterized by cell activation and adhesion, inflammation and/or toxemia, that is one or more of these phenomena are occurring in the animal and are the object of treatment with the liposomal formulations of this invention. This method comprises administering to the animal an amount of the liposome which comprises an anti-disorder effective amount of the arachidonic acid metabolite.

Disorders which can be treated with the formulations of this invention include, without limitation: reperfusion injury, systemic inflammatory response syndrome (SIRS), myocardial infarction, adult respiratory distress syndrome (ARDS), vasculitis, post-traumatic shock, burn injuries, vaso-occlusive disorders, arthritic disorders, such as rheumatoid and filary arthritis and gout, and auto-immune disorders, for example, systemic lupus erythematosus, juvenile diabetes, multiple sclerosis or Hashimoto's thyroiditis. Particularly preferred indications are ARDS and SIRS.

Generally, the anti-disorder effective amount of the arachidonic acid metabolite is at least about $10^{-12}$ g of the metabolite per kg of body weight of the animal. Typically, the effective amount is from about $10^{-12}$ g of the metabolite per kg of body weight of the animal to about $10^{-3}$ g per kg. Preferably, the effective amount is from about $10^{-18}$ g of the metabolite per kg of body weight of the animal to about $10^{-4}$ g per kg. More preferably, the effective amount is about $10^{-6}$ g of the metabolite per kg of body weight.

The method of this invention can comprise administering to the animal an additional bioactive agent, for example, an antimicrobial or anti-inflammation agent; this additional agent is typically selected by means, and for reasons, well understood by ordinarily skilled artisans given the teachings of this invention. The additional bioactive agent can be an additional arachidonic acid metabolite.

μg/kg PGE$_1$ or equivalent amount of placebo liposomes; unshaded: 50 μg/kg; lightly shaded: 10 μg/kg.

Figure 5:
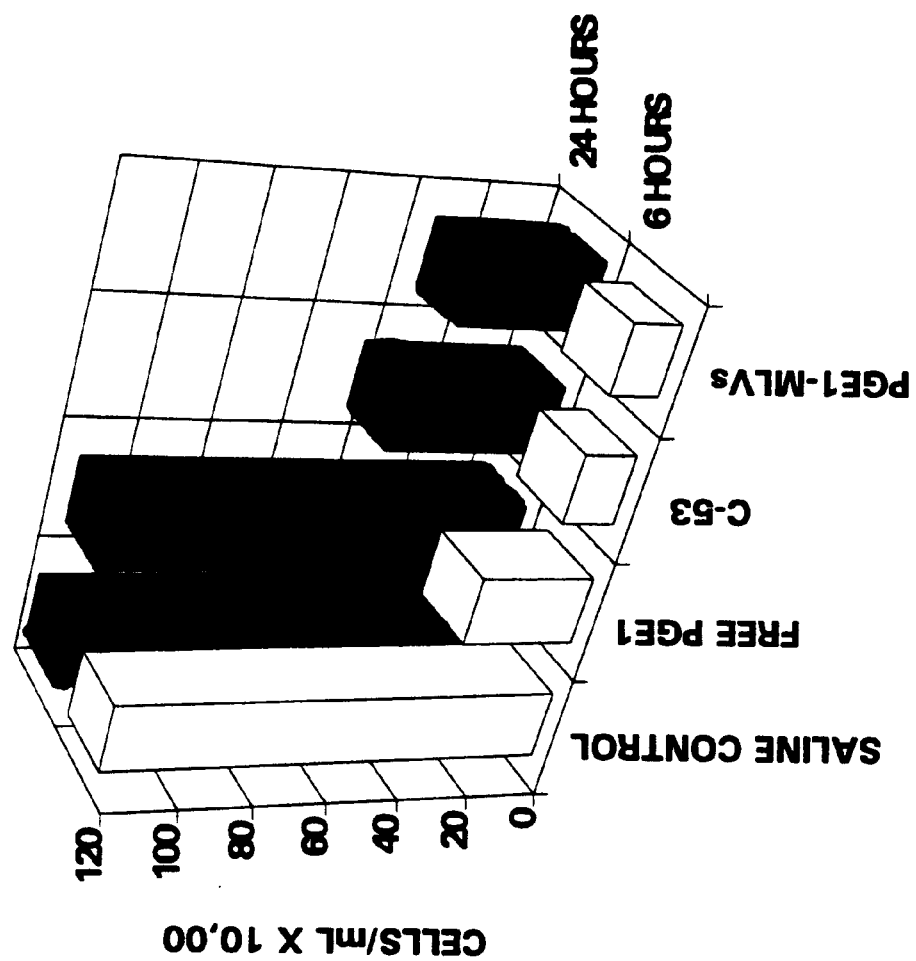

FIG. 5. Extended Inhibition of Extravasation. Male Sprague-Dawley rats were treated as described above. After six and 24 hours, the air pouch exudates were collected, and the air pouch total cell populations were determined. The figure is scaled for prostaglandins. The values for the six-and 24-hour saline controls (200 and 925, respectively) are off the scale of the figure. For each treatment group, n=4. X-axis: Saline control, free PGE$_1$, C-53 and MLV-PGE$_1$; y-axis: cells/ml×10,000; z-axis: six- (unshaded) and 24-hour (shaded) treatments.

Figure 6:
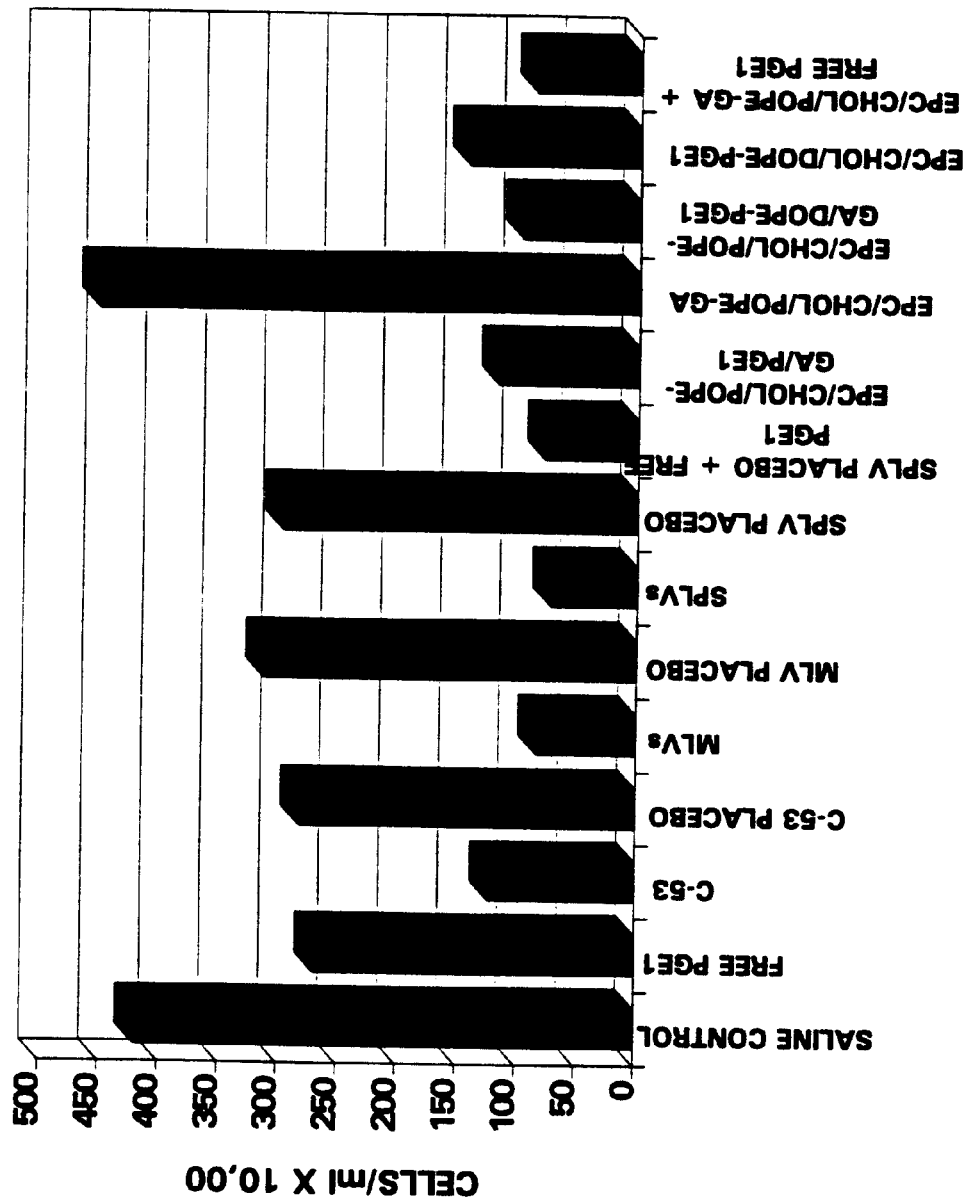

FIG. 6. Inhibition of Extravasation by Alternative Liposomal Formulations. Male Sprague-Dawley rats were treated as described above. For each treatment group, n=4. X- axis: saline control, free PGE$_1$, C-53, C-53 placebo, MLV-PGE$_1$, MLV placebo, SPLV-PGE$_1$ (stable plurilamellar vesicle, see Lenk et al., U.S. Pat. Nos. 4,522,803, 5,030,453 and 5,169,637), SPLV placebo, SPLV placebo plus free PGE$_1$, EPC/Cholesterol (Chol)/POPE-GA (1-palmitoyl-2-oleoyl-phosphatidylcholine—glutaric acid)-PGE$_1$, EPC/Chol/POPE-GA (no PGE$_1$), EPC/Chol/POPE-GA/DOPE-PGE$_1$ (dioleoyl phosphatidylethanolamine covalently linked to PGE$_1$), EPC/Chol/DOPE-PGE$_1$, EPC/Chol/POPE-GA placebo plus free PGE $_1$; y-axis: cells/ml× 10,000.

Figure 7:
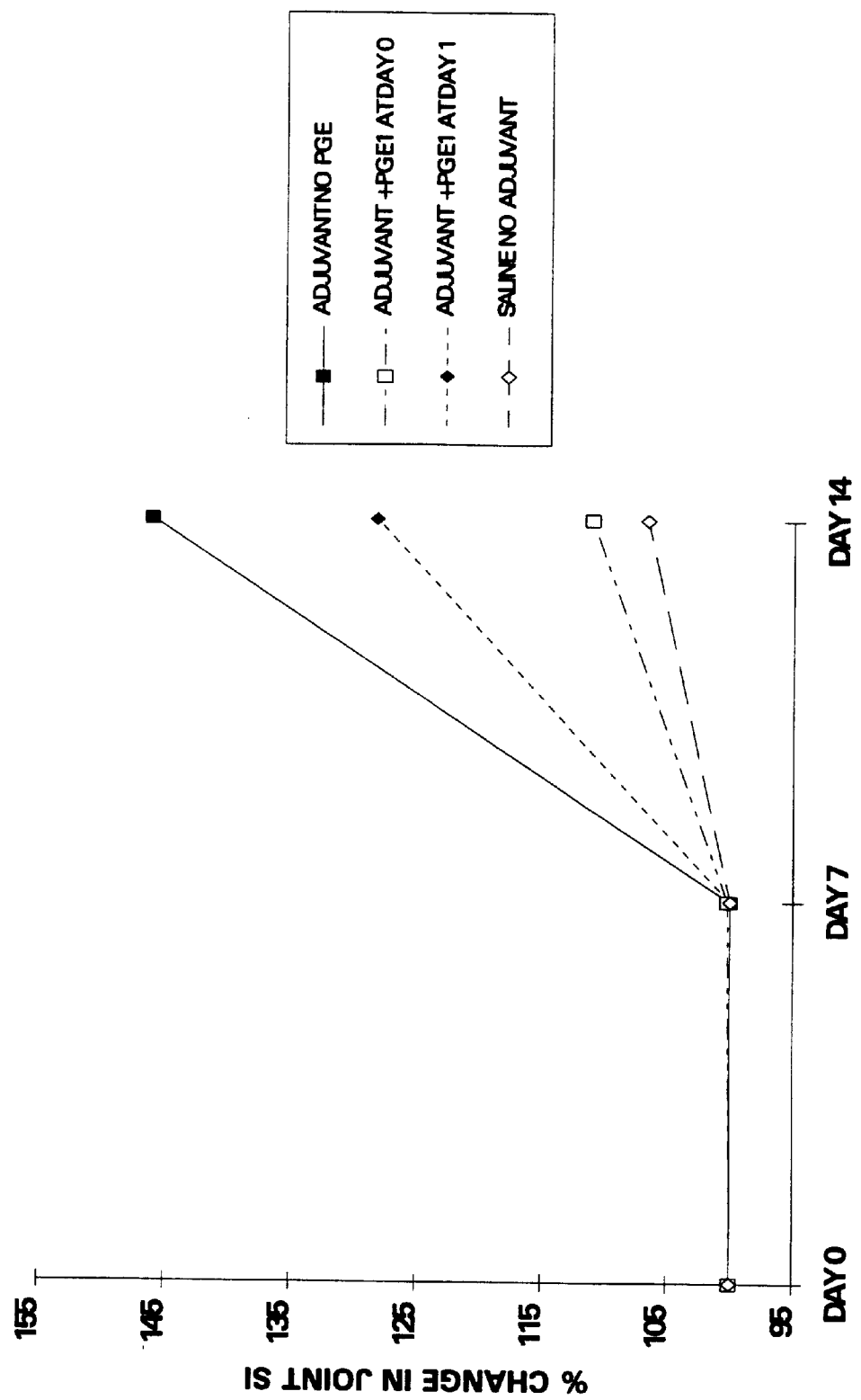

FIG. 7. Adjuvant Arthritis/Free PGE$_1$. Male Lewis rats were inoculated at day 0 with complete Freund's adjuvant, as described hereinbelow. Free PGE$_1$ was injected into one group of rats, at a dose of 10 μg/kg, beginning at day 0, with the injections repeated every second day. Free PGE$_1$ was also injected into another group, at a dose of 10 μg/kg, beginning at day 10, and repeated every second day. Also administered was an adjuvant control (no PGE$_1$) and a saline control (no adjuvant). For each treatment group, n=6. X-axis: time (days); y-axis: % change in jaw size. Filled squares: adjuvant control (no PGE$_1$); open squares: adjuvant and PGE$_1$ administered at day 0; filled diamonds: adjuvant administered at day 0, PGE$_1$ at day 10; open diamonds: saline control (no adjuvant).

Figure 8:
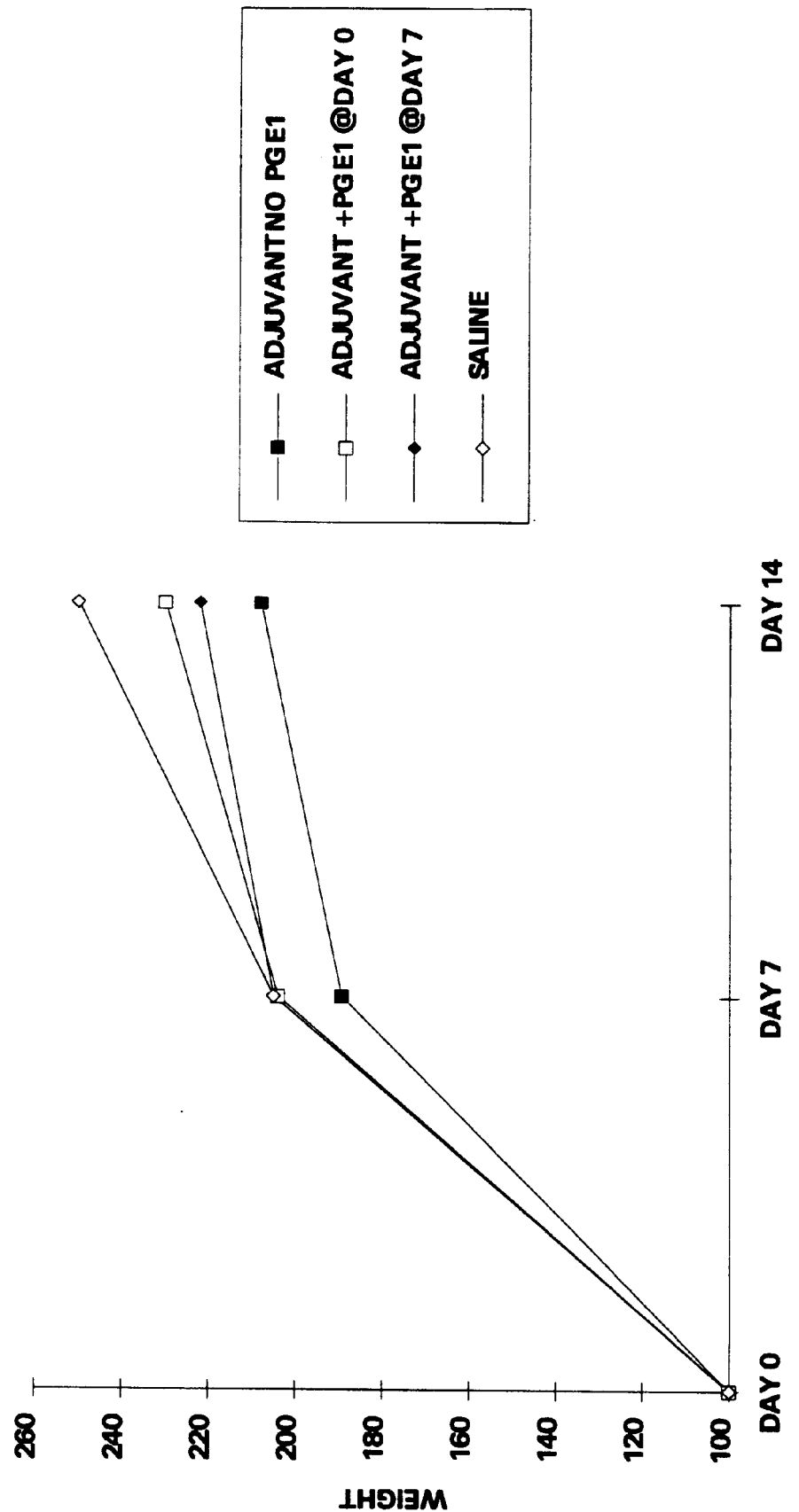

FIG. 8. Adjuvant Arthritis/Free PGE$_1$. Male Lewis rats were treated as described above with complete Freund's adjuvant and PGE$_1$. Animal weight during the treatment period was assessed weekly. For each treatment group, n=6. X-axis: time (days) post-adjuvant administration; y-axis: weight %. Filled squares: adjuvant control; open squares: adjuvant plus PGE$_1$ at day 0; filled diamonds: adjuvant plus PGE$_1$ at day 10; open diamonds: saline control.

Figure 9:
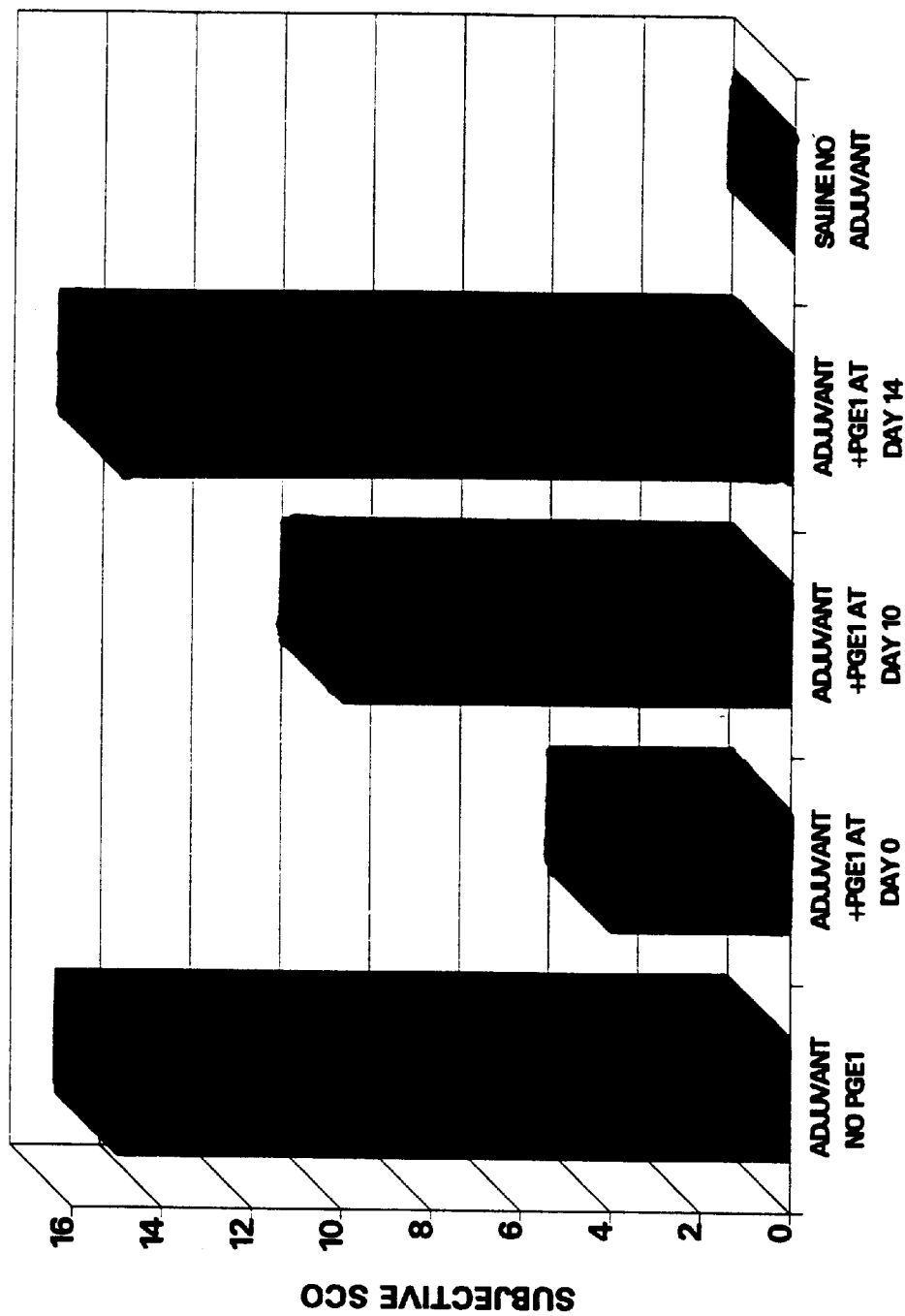

FIG. 9. Rat General Health/Motility. Male Lewis rats were treated as described above with complete Freund's adjuvant and PGE$_1$. Animal general health, vigor and motility were subjectively scored at day 14 of the treatment period. For each treatment group, n=6. X-axis: adjuvant control, adjuvant plus PGE$_1$ at day 0, adjuvant plus PGE$_1$ at day 10, adjuvant plus PGE$_1$ at day 14, saline control (no adjuvant), y-axis: subjective score.

Figure 10:
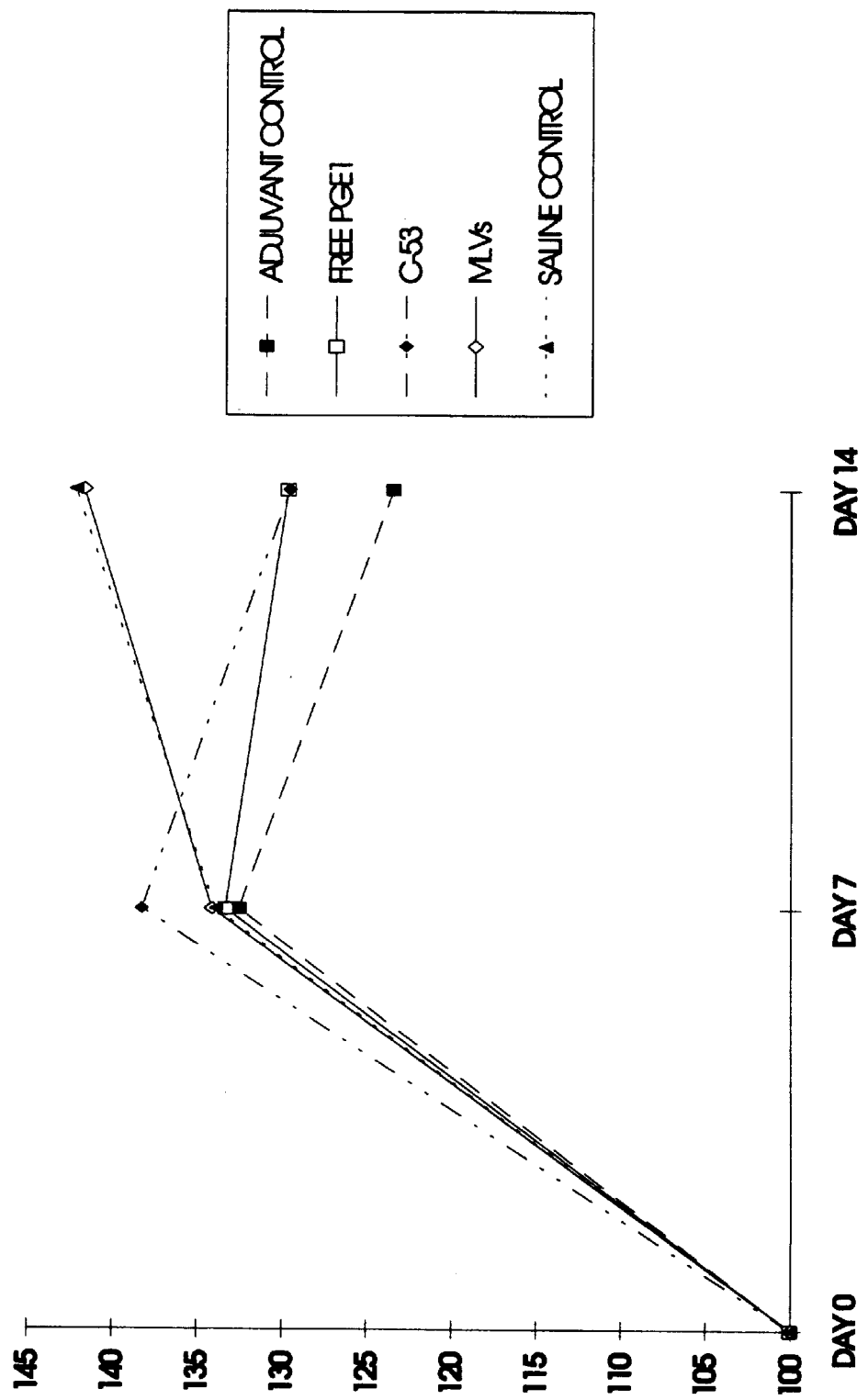

FIG. 10. Adjuvant Arthritis/Liposomal PGE$_1$. Male Lewis rats were treated, as described above with complete Freund's adjuvant, and PGE$_1$ at a dose of 10 μg/kg of body weight. The rats were administered an adjuvant alone (filled triangles), the adjuvant and free (unentrapped) PGE$_1$ (filled squares, upper line), the adjuvant and multilamellar liposomal PGE$_1$ (filled squares, lower line) and a saline control with no adjuvant (filled circles). X-axis: time (days) post-adjuvant treatment; y-axis: percent change in paw size.

Figure 11:
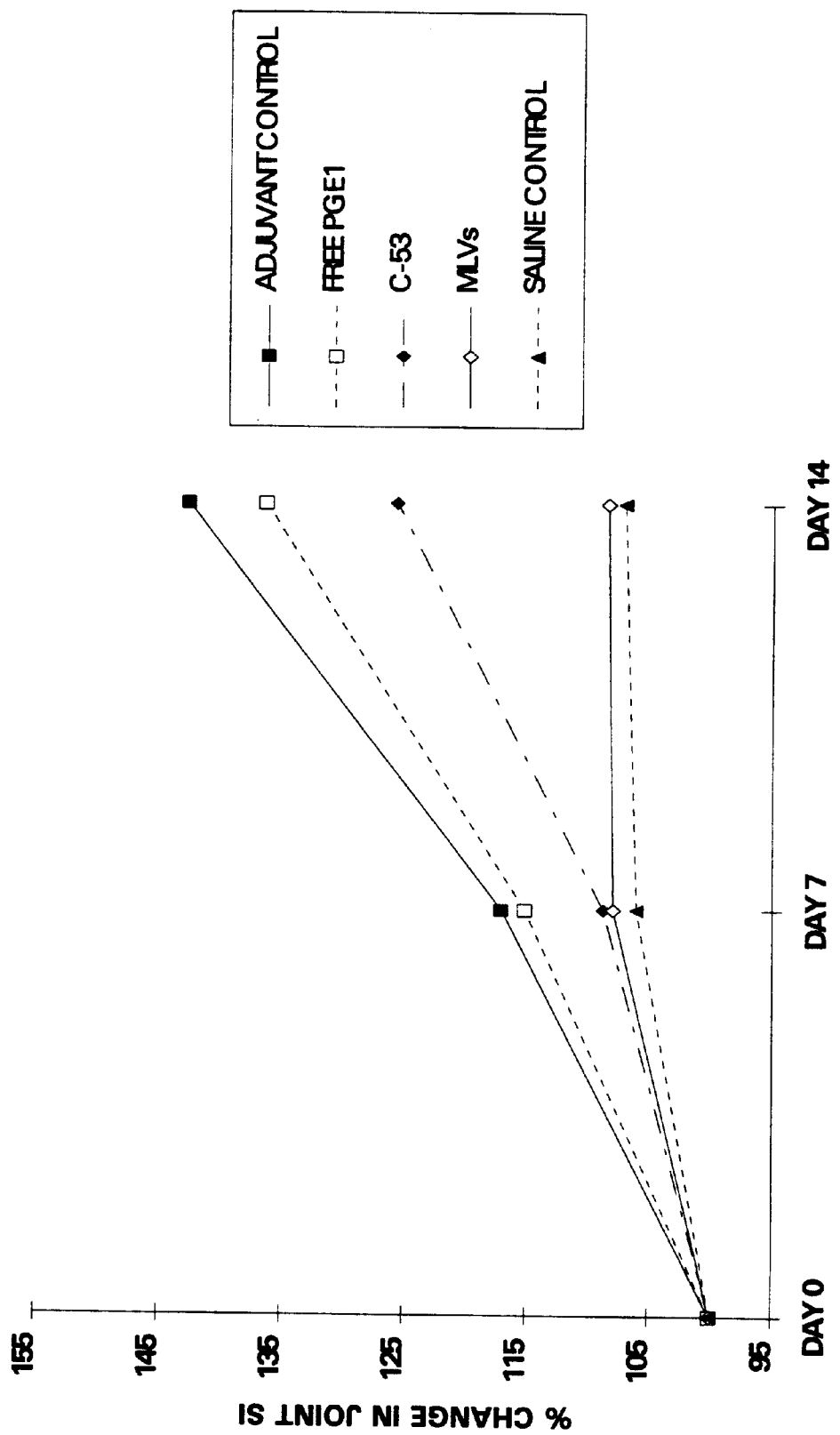

FIG. 11. Adjuvant Arthritis/Liposomal PGE$_1$. Male Lewis rats were treated as described above with free or liposomal PGE$_1$ at a dose of 10 μg/kg. Joint diameter was assessed weekly. For each treatment group, n=6. The rats were administered an adjuvant control (no PGE$_1$; filled squares), adjuvant plus free PGE$_1$ (open squares), adjuvant plus C-53 (filled diamonds), adjuvant plus PGE$_1$-MLVs(open diamonds) or a saline control (no adjuvant). X-axis: time (days) post-adjuvant treatment; y-axis: percent change in paw size.

Figure 12:
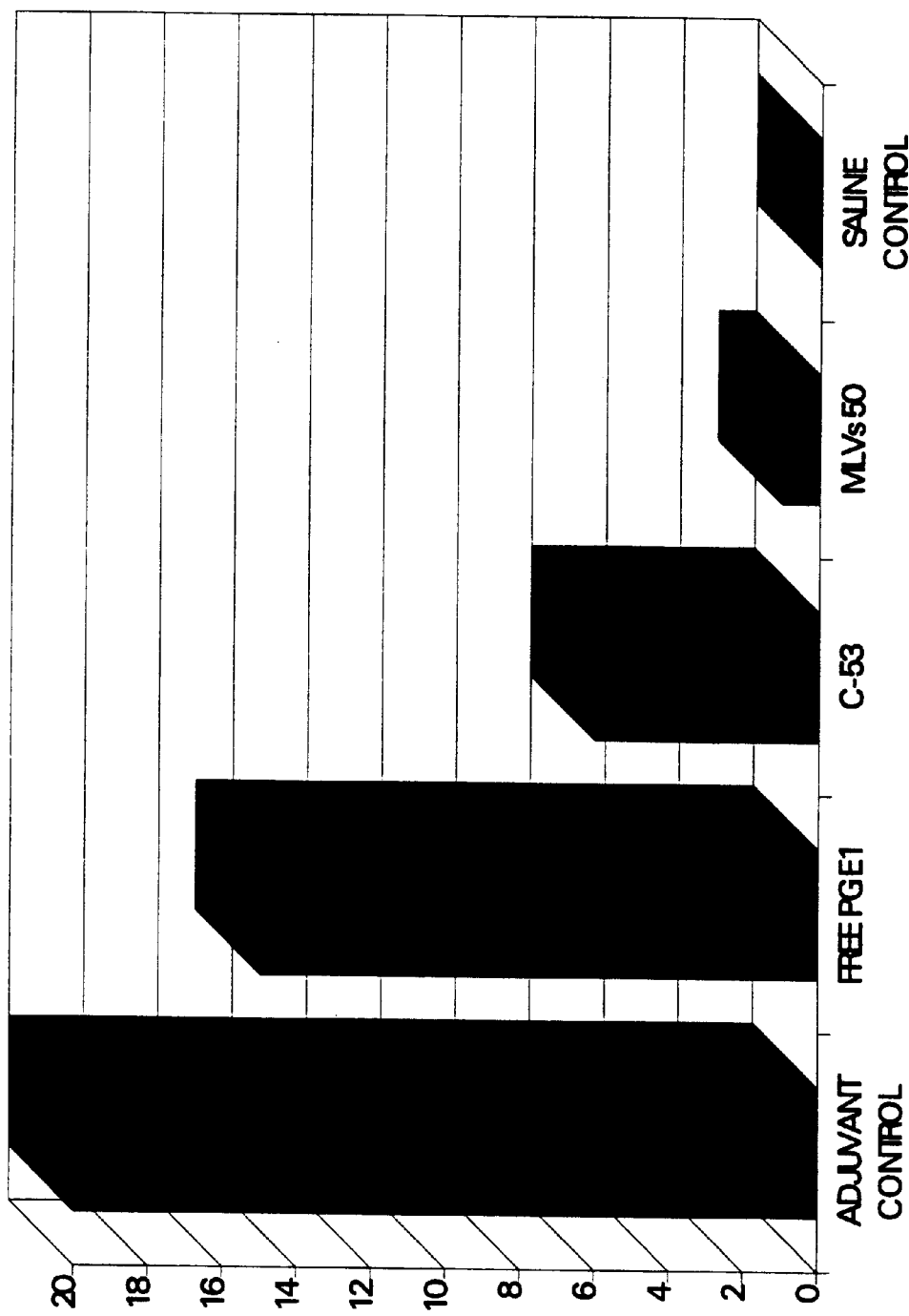

FIG. 12. Adjuvant Arthritis/Liposomal PGE$_1$. Male Lewis rats were treated as described above with free or liposomal PGE$_1$ at a dose of 10 μg/kg. Animal general health, vigor and motility were subjectively scored at day 14 post-adjuvant treatment. For each treatment group, n=6. X-axis: adjuvant control, free PGE$_1$, C-53, PGE$_1$-MLVs, saline control; y-axis: subjective score.

Figure 13:
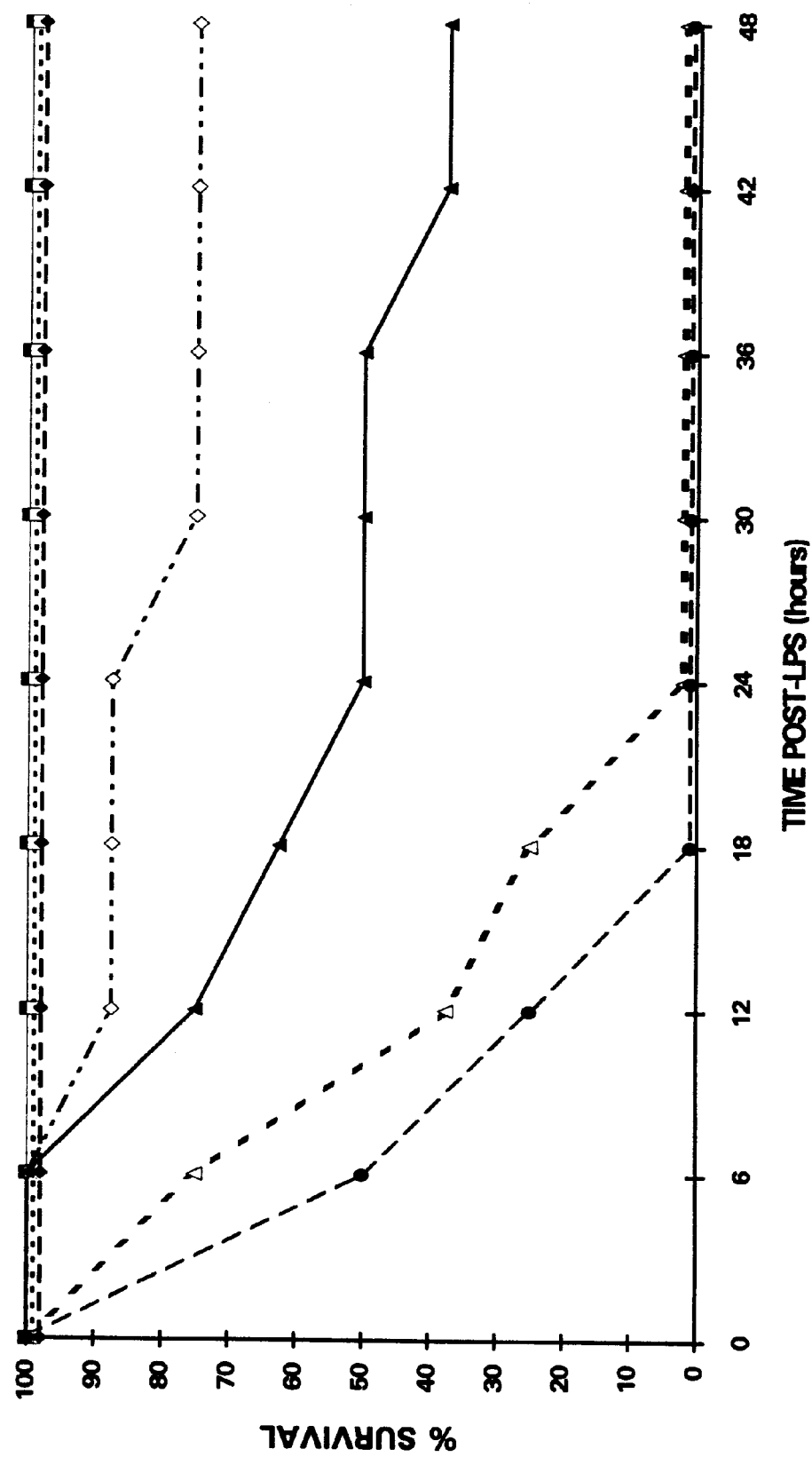

FIG. 13. Rat Endotoxemia Model. Male Sprague-Dawley rats, weighing 126–150 g each, were acclimated for two days in an animal facility with food and water ad libitum. At time 0, groups of rats (n=16) were injected i.v. with either *E. coli* lipopolysaccharide (LPS; serotype 055:B5) as a single bolus, or with a saline (no LPS) control. Mortality was assessed at the indicated times (days) post-LPS administration. X-axis: time (days) post-LPS administration; y-axis: percent survival in treatment group. Filled squares: rats administered saline control (0 μg/kg LPS); open squares: rats administered 10 μg/kg LPS; filled diamonds: 15 μg/kg LPS; open diamonds: 25 μg/kg LPS; filled triangles: 50 μg/kg LPS; open triangles: 75 μg/kg LPS; filled circles: 100 μg/kg LPS.

FIG. 14. Rat Endotoxemia Model/Liposomal Prostaglandin Treatment, Male Sprague-Dawley rats were injected i.v. with 50 μg/kg LPS at time 0. Free or liposomal PGE$_1$ (40 μg/kg) was simultaneously injected i.v. Survival in the treatment groups (n=12) was assessed at the indicated times. X-axis: time (days) post-LPS administration; y-axis: percent survival in treatment group. Filled squares: saline control (no LPS); open squares: free PGE$_1$; filled diamonds: C-53; open diamonds: PGE$_1$-MLVs; filled triangles: LPS control (no PGE$_1$).

DETAILED DESCRIPTION OF THE INVENTION

This invention provides a multilamellar liposome which comprises an arachidonic acid metabolite, two or more lipid bilayers comprising a lipid and two or more compartments comprising a release-inhibiting aqueous buffer.

Liposomes are self-assembling structures comprising one or more bilayers of amphipathic lipid molecules, each of which encloses an internal compartment. The amphipathic lipid molecules which make up lipid bilayers comprise a polar (hydrophilic) headgroup region covalently linked to one or two non-polar (hydrophobic) acyl chains. The energetically unfavorable contact between the hydrophobic acyl chains and the aqueous medium causes the lipid molecules to rearrange such that the polar headgroups are oriented towards the aqueous medium while the acyl chains reorient towards the interior of the bilayer. The net result is an energetically stable structure in which the acyl chains are effectively shielded from coming into contact with the aqueous medium. Unilamellar liposomes have a single lipid bilayer.

Multilamellar liposomes have two or more bilayers. Multiple lipid bilayers generally present numerous barriers through which an arachidonic acid metabolite may have to pass in order to leak from the liposome into the external environment. Furthermore multiple lipid bilayers are likely to be able to maintain the internal pH of the liposome for a longer period of time than a single lipid bilayer; internal pH can be a factor in determining the length of time an arachidonic acid metabolite is associated with a liposome.

Multilamellar liposomes can be produced by a variety of methods (for a review, see, e.g., Cullis et al., in: Liposomes, From Biophysics to Therapeutics (M. J. Ostro, ed.), Marcel Dekker, pp. 39–72 (1987)). Bangham's procedure (J. Mol. Biol. 13:238 (1965)) produces "ordinary" multilamellar vesicles (MLVs). The process involves dissolving one or more amphiphilic lipids in one or more organic solvents. The lipids are then dried, and the dried lipids are rehydrated with an aqueous solution so as to form the MLVs. These "ordinary" MLVs typically have unequal distribution of a solute amongst their aqueous compartments. Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having a solute entrapped in their aqueous compartments, wherein the distribution of the solute in each of the compartments is substantially equal. Substantially equal interlamellar solute distribution generally means that there is less osmotic stress in these multilamellar liposomes than in "ordinary" MLVs. The multilamellar liposome of this invention preferably has substantially equal interlamellar solute distribution.

The multilamellar liposome of this invention is typically less than about 5 microns in diameter, and is preferably less than about 1 micron in diameter. More preferably, the liposome is from about 500 nm in diameter to about 1 micron in diameter. Liposomes can be size reduced by a number of methods well known to, and readily practiced by, ordinarily skilled artisans, for example extrusion under pressure one or more times through filters having defined pore sizes (see Cullis et al., U.S. Pat. No. 5,008,050; and Loughrey et al. (U.S. Pat. No. 5,059,421). Liposome size can be determined by a number of methods well known to, and readily practiced by, ordinarily skilled artisans, for example freeze-fracture electron microscopic examination of liposomes, and quasi-electric light scattering.

Liposomes can be loaded with bioactive agents by solubilizing the molecule in the medium in which the liposomes are formed, in the case of water-soluble agents, or adding lipid-soluble agents to the lipid solutions from which the liposomes are made. Ionizable bioactive agents can also be loaded into liposomes by establishing an electrochemical potential gradient across the liposomal membrane and then adding the agent to the medium external to the liposome.

Prostaglandins are a group of twenty-carbon fatty acids containing a five-carbon ring, plus seven- and eight-carbon chains. Prostaglandins are generally made from other twenty-carbon fatty acid precursors having at least three double bonds, i.e., essential fatty acids (e.g., 8,11,14-eicosatrienoic acid, 5,8,11,14-eicosatetraenoic acid or 5,8, 11,14,17-eicosapentanoic acid; see, e.g., Goodman and Gilman's The Pharmacological Basis of Therapeutics, supra). Arachidonic acid is the most abundant of these twenty-carbon prostaglandin precursors in humans.

Intermediates, such as prostanoic acids are generally formed during the conversion of such precursors to prostaglandins. Compounds such as leukotrienes, thromboxanes, lipoxins and prostacyclins are functionally related to prostaglandins, can also be derived from the twenty carbon essential fatty acid prostaglandin precursors, and may be eicosanoids. Prostaglandins, prostaglandin precursors, intermediates formed during prostaglandin synthesis, prostaglandin-related compounds and eicosanoids are "arachidonic acid metabolites."

Prostaglandins are the preferred arachidonic acid metabolites. The various prostaglandins are classified in several major groups (A–I) according to the arrangement of substituents on the five-carbon rings; these groups can be further subdivided based on the number, and position, of double bonds in the prostaglandins' carbon chains. Preferred prostaglandins are E series or I series prostaglandins; most preferably, the prostaglandin is $PGE_1$.

"Association" of an arachidonic acid metabolite with a liposome generally means that the metabolite is entrapped in an aqueous compartment of the liposome, or is associated with the inner or outer monolayer of a lipid bilayer, for example by way of electrostatic interactions between the metabolite and the headgroups of the monolayer's component amphipathic lipids.

The multilamellar liposome of this invention preferably has a bilayer comprising a lipid which tends to increase the strength of arachidonic acid metabolite-lipid interactions, and thereby inhibit release of the metabolite from the liposome. Such lipids may be referred to as "release-inhibiting lipids." Lipid based factors which tend to increase the strength of prostaglandin-lipid interactions include, but are not limited to, those factors which tend to make lipid bilayers less permeable to water and other small molecules, e.g., those factors which tend to increase Van der Waals, dipole-dipole and other interactions between acyl chains and hence, make acyl chains pack more closely together in the bilayer. For example, the number of double bonds in the bilayer's acyl chains can affect the chains' arrangement with respect to each other in the bilayer. The lower the number of double bonds, the more closely acyl chains are likely to pack together, and hence, are more likely to present a barrier to a prostaglandin transiting the bilayer. Accordingly, preferred release-inhibiting lipids have saturated acyl chains. The saturated acyl chain lipid can be dipalmitoyl phosphatidylcholine (DPPC); however, other saturated chain lipids can also be used.

Aqueous buffers in liposomes can also inhibit or prevent release of an arachidonic acid metabolite associated with a liposome. Such aqueous buffers are "release-inhibiting aqueous buffers." Characteristics of preferred release-inhibiting buffers include, but are not limited to the ability to establish electrostatic repulsions with prostaglandins and thereby enhance prostaglandin-lipid interactions, or otherwise to increase the strength of such interactions. Furthermore, buffers with a higher buffering capacity, and hence a greater ability to maintain the desired pH, will be better release-inhibiting buffers. Preferred release-inhibiting buffers are citric acid buffers, particularly those citric acid buffers having a pH of about 4.5.

The multilamellar liposome of this invention can comprise a drying protectant, which is generally a hydrophilic compound, such as a saccharide, urea, dextran, albumin or polyvinyl alcohol, capable of preventing the rearrangement of the lipids in the liposomes, so that when the liposomes are reconstituted subsequent to dehydration, a substantial portion of the contents originally entrapped in the liposomes remain therein. Drying protectants are generally strong hydrogen bond acceptors, and typically possess stereochemical features favorable to preserving the intramolecular spacing of the bilayer constituents, Saccharides, such as mannose, galactose, trehalose, raffinose, maltose, sucrose, lactose or dextrose are preferred drying protectants. Maltose is particularly preferred.

Saccharides such as maltose are typically used as drying protectants at concentration of from about 5 to about 20 percent, preferably at about 10 percent by weight of the aqueous phase used to prepare liposomes. Mannitol may be used in conjunction with any of the saccharides, but it has surprisingly been found that when used alone, mannitol does not succeed in maintaining liposome size. Mannitol may be used in concert with the saccharides in about a 0–2%, preferably a 1%, weight-by-volume of aqueous phase concentration. The total concentration of saccharide used ranges from about 5% to about 20%, preferably 10% to 12%, most preferably about 10%. Additional preservatives such as BHT or EDTA in the formulations at, for example, 5 mg BHT per ml of ethanol, and, for example, 0.01% EDTA in 10% dextrose may also be included.

Preferably, the multilamellar liposome of this invention comprises $PGE_1$, two or more lipid bilayers comprising a release-inhibiting lipid, two or more aqueous compartments comprising a citric acid buffer having a pH of about 4.5, and has substantially equal interlamellar solute distribution. Particularly preferred multilamellar liposomes comprise a drying protectant, e.g., maltose.

The multilamellar liposome of this invention can comprise an additional bioactive agent, i.e., a bioactive agent in addition to the arachidonic acid metabolite associated with the liposome. "Bioactive agent" as used herein denotes any compound or composition of matter which can be administered to animals. These include agents having biological activity in the animals, as well as those useful for imaging or other forms of diagnosis. Bioactive agents include, but are not limited to: antiviral, antibacterial, antifungal, antiparasitic, antimetabolic, antiglaucomic, antiinflammatory or antineoplastic compounds, sterols, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, vasodilators, bronchodilators, local anesthetics, growth promoting agents, regenerative agents and the like. This additional bioactive agent can be an additional arachidonic acid metabolite.

The multilamellar liposome of this invention can comprise a headgroup-modified lipid. Liposomes are cleared from an animal's body by way of its reticuloendothelial system (RES) which consists of fixed and circulating macrophages. Avoiding RES clearance allows liposomes to remain in the circulation longer, meaning that less of the drug need be administered to achieve desired serum levels. Enhanced circulation times also allow targeting of liposomes to non-RES containing tissues. Liposomal surfaces become coated with serum proteins when administered to animals. Rates of clearance by the RES can be related to the rate and level of such protein coating; accordingly, clearance can be inhibited by modifying the outer surface of liposomes such that binding of serum proteins is generally inhibited. This can be accomplished by minimizing or shielding negative surface charges, which can promote protein binding, or by otherwise presenting a steric hindrance to the binding of serum proteins.

Effective surface modification, that is, alterations to the outer surfaces of liposomes which result in inhibition of RES uptake, can be accomplished by incorporating headgroup-modified lipids into liposomal bilayers. "Headgroup-modified lipids" as used herein are amphipathic lipids whose polar headgroups have been derivatized by attachment thereto of a chemical moiety, e.g., polyethylene glycol, a polyalkyl ether, a ganglioside, an organic dicarboxylic acid, e.g., glutaric acid, or the like, which can inhibit the binding of serum proteins to liposomes such that the pharmacokinetic behavior of the vesicles in the circulatory systems of animals is altered (see, e.g., Blume et al., Biochim. Biophys. Acta. 1149:180 (1993); Gabizon et al., Pharm. Res. 10(5):703 (1993); Park et al. Biochim. B Acta. 1108: 257); Woodle et al., S. Patent No. 5,6; Allen et al,, U. Patent Nos. 4,8 and 4,920,016).

The liposome of this invention can further comprise a headgroup-modified lipid, the concentration of which in the liposome's bilayers depends upon a number of factors well known to the ordinarily skilled artisan, or within his purview to determine without undue experimentation, given the teachings of this invention. These include: the type and size of the liposome; and the intended therapeutic use of the liposomal formulation. Typically, the concentration of the headgroup-modified lipid in the liposome is at least about five mole percent, desirably, about ten mole percent.

Also provided herein is a dehydrated multilamellar liposome comprising an arachidonic acid metabolite and two or more lipid bilayers comprising a lipid. Liposomal dehydration enables liposomes to be stored for extended periods of time; they can then be reconstituted on an as-needed basis. Liposomes can be dehydrated, with freezing, using standard freeze-drying equipment, or its equivalents. Lyophilization is preferably carried out after incorporating one or more drying protectants, generally hydrophilic compounds such as sugars, into liposome preparations in accordance with the procedures of Schneider et al. (U.S. Pat. No. 4,229,360) and Janoff et al., (U.S. Pat. No. 4,880,635); the contents of which are incorporated herein by reference). The protective sugar, e.g., maltose, sucrose, dextrose, raffinose, trehalose, lactose or galactose, but preferably maltose, can be omitted if the dehydration is conducted without prior freezing and sufficient water is left remaining in the liposomal preparation to maintain the integrity of a substantial portion of the liposomal bilayers through the dehydration-rehydration process. The dehydrated multilamellar liposome of this invention can comprise a drying protectant.

This invention provides a two-component system which comprises an aqueous solution and a dehydrated multilamellar liposome comprising an arachidonic acid metabolite and two or more lipid bilayers comprising a lipid. The aqueous solution and the dehydrated multilamellar liposome are combined so as to rehydrate or reconstitute the dehydrated liposome. The aqueous solution can be a number of solutions including the pharmaceutically acceptable carriers, e.g., aqueous buffered solutions, disclosed herein. The components can be provided in vials or other packaging in which it is convenient to store and combine the components.

Further provided herein is a pharmaceutical composition comprising a pharmaceutically acceptable carrier and the multilamellar liposome of this invention. "Pharmaceutically acceptable carrier" as used herein means any of the standard carriers, diluents, excipients and the like generally intended for use in connection with the administration of bioactive agents to animals, particularly humans, Such carriers are well known in the art and are generally chosen with regards to a number of factors, such as the particular drug being used and the intended route of administration, which are well understood by the ordinarily skilled artisan, or are within his purview to determine without undue experimentation. Suitable carriers include, but are not limited to salt solutions such as physiological saline, aqueous dextrose solutions, e.g., D5W, water for injection (WFI), and the like. The pharmaceutical composition can further comprise auxiliary agents such as preservatives, anti-oxidants and the like in amounts, and for reasons, well known to the ordinarily skilled artisan.

This invention provides a method of administering an arachidonic acid metabolite to an animal, preferably a human, the method comprising administering to the animal a composition comprising a pharmaceutically acceptable carrier and a multilamellar liposome comprising the metabolite. The metabolite is preferably $PGE_1$. The liposome comprises two or more bilayers comprising a lipid, preferably a saturated acyl chain lipid, and two or more compartments comprising an aqueous release-inhibiting buffer, preferably a citric acid buffer having a pH of about 4.5. Preferably, the multilamellar liposome has substantially equal interlamellar solute distribution. The liposome-containing composition is preferably administered intravenously.

This method can be used to treat an animal afflicted with a disorder characterized by cell activation and adhesion, inflammation and/or toxemia. That is, one or more of these phenomenon can be ameliorated, lessened, alleviated, inhibited or prevented by administration of the formulations of this invention to an afflicted animal. Disorders to which the present invention may be directed include, without limitation: reperfusion injury, systemic inflammatory response syndrome (SIRS), adult respiratory distress syndrome (ARDS), myocardial infarction, vasculitis, burn injuries, restenosis after angioplasty and other vaso-occlusive disorders, arthritic disorders, for example, gout, rheumatoid arthritis and filary arthritis, and auto-immune disorders, for example, systemic lupus erythematosus, juvenile diabetes, multiple sclerosis, and Hashimoto's thyroiditis. Particularly preferred indications are SIRS and ARDS.

Certain disorders are characterized by the abnormal activation of cells, e.g., platelets and neutrophils, in the blood, and by the subsequent adhesion of these cells to each other or to activated cells in the surrounding vascular endothelium. Endothelial cells, for example vascular, plural, pericardial or abdominal endothelial cells, can be activated by cytokines, e.g., interleukin-1 (IL-1), tumor necrosis factor-alpha (TNF-alpha) or bacterial endotoxins. In like manner, blood cells, particularly neutrophils and platelets, can be activated by agents such as GM-CSF, bacterial endotoxins, bacterial chemoattractants, TNF-alpha and the C5$a$ component of complement. Activated cells have adhesion sites on their surfaces by which they can adhere to each other. Activated and adhered cells can form clumps, which can clog small blood vessels such as those found in the lungs and heart, and thereby reduce blood flow to surrounding tissue. The activated cells can also adhere to activated vascular endothelial cells; such adhesion can lead to subsequent degranulation of vascular endothelium, or to the release of mediators of cell damage, such as superoxide anion ($O_2^-$) and proteolytic enzymes.

Reperfusion of occluded blood vessels, or incidental to surgery in which blood flow is temporarily stopped, is addressed in Seewaldt-Becker et al., "Effect of Anti-Adhesive Antibodies on Reperfusion Injury," in: Leukocyte Adhesion Molecules, Springer-Verlag, New York (1990) pp. 138–148; and "Adhesion in Disease and Therapy," (Springer et al., eds.), in: Leukocyte Adhesion Molecules, Springer-Verlag, New York (1990), pp. 85–156). When there is a blockage in a blood vessel, surrounding endothelial cells, as well as downstream ischemic tissue, can be damaged. There can even be further damage to nearby endothelial cells when the occlusion is cleared. Such damaged cells can in turn induce activation in neutrophils and platelets after restoration of blood flow to the affected areas.

When patients are subject to the insults that can lead to ARDS, such as, to trauma, surgically or otherwise induced, burns, sepsis, aspiration and hyperoxia, many organs in the body other than the lungs can be affected. The causes and clinical courses of this condition can vary widely. For example, in the case of a patient with a severe toxemia, bacterial endotoxins can be released from bacterial cell wall; such release can initiate the inflammatory cascade, leading to septic shock.

Angioplasty is a technique whereby a balloon is inserted into an occluded artery and inflated in order to open blocked blood vessels. Although this technique has become quite routine in the management of coronary artery disease in the six month period following this procedure, over 33% of the treated patients experience restenosis, or reocclusion of the previously opened blood vessel. It is thought that this condition starts with injury to the vascular endothelium which often results form the balloon procedure. The exposed extracellular matrix will rapidly bind to several layers of activated platelets. Once platelets bind, they will release a variety of growth factors which will result in the proliferation of smooth muscle cells underlying the vessel to the point where the vessel becomes reoccluded. By preventing platelets from binding to the extracellular matrix, one can disrupt the cascade of events resulting in restenosis. Thus, acute administration at the time of the angioplasty procedure of a drug that prevents platelet adhesion could prevent restenosis.

Recently, De Servi et al., European Heart Journal, "Prostaglandin E administration in unstable angina patients undergoing PTCA; preliminary results", August 1990., published the results of a clinical trial in patients with unstable angina who were given an intracoronary infusion of $PGE_1$ prior to and following angioplasty. The drug was infused over a 24-hour period. The results of this study showed that the rate of restenosis six months after angioplasty in the $PGE_1$-treated group was reduced by almost 50% verses the untreated control group, even though the treatment with $PGE_1$ only lasted 24 hours.

Acute myocardial infarction (more commonly referred to as a heart attack) refers to a blockage of the blood supply to the muscles of the heart, usually caused by a blood clot. If the blood is prevented from reaching the heart for too long, the patient will die. When an occlusion of the coronary artery occurs, the patient is either treated with a fibrinolytic agent, such as tissue plasminogen activator (tPA) or streptokinase, to dissolve the clot, or the blockage may resolve itself. In both instances, blood flow is resumed to the ischemic (oxygen-deprived) region of the heart. This reflow of blood into the heart is called reperfusion. While reperfusion is necessary to save the patient's life, it causes further injury to the heart muscle called reperfusion injury. Reperfusion injury is known to be the end result of the inflammatory cascade.

In addition to the problem of reperfusion injury following clot removal, patients suffering from a myocardial infarction may suffer from other secondary problems. For example, after the normal blood flow is restored to the heart, both neutrophils and platelets are activated. Activated platelets often adhere to one another and begin to reocclude the coronary artery, resulting in a situation where the rate of blood flowing to the heart decreases over time. In some cases, complete reocclusion will occur.

Sharma et al., The American Journal of Cardiology, "Intracoronary Prostaglandin $E_1$ Plus Streptokinase in Acute Myocardial Infarction", page 1161, Dec. 1986, vol. 58, has shown in a clinical setting of acute myocardial infarction that administration of free $PGE_1$ by slow intracoronary infusion together with intracoronary streptokinase provides positive clinical results when compared with a control group taking intracoronary streptokinase alone. The results showed decreased time to reperfusion, reduced dose of streptokinase required, increased percentage of vessels patent after 10 days, and higher ejection fractions. Drawbacks of the study are that the drug must be given by slow intracoronary infusion which is cumbersome and requires specialized facilities and highly trained personnel. Also this approach requires careful titration of the dose of $PGE_1$ so that significant drops in blood pressure can be seen.

Inflammatory responses include local reactions and resulting morphological changes, destruction or removal of injurious materials and activation of repair mechanisms. Inflammation can be part of the process by which animals heal themselves, but it can also occur in response to abnormal physiological stimuli and can cause problems in the body. Joints, for example, become inflamed in arthritic conditions such as gout, filary arthritis, rheumatoid arthritis and Lyme disease (see, e.g., Stedman's Medical Dictionary (Illustrated), supra at pages 123–124). These states may be characterized by the extravasation of cells, i.e, the egress of cells from the circulation into the inflamed area.

Toxemia is the clinical manifestations observed during the course of infections by infectious agents, e.g., microbes which contain toxins and other substances poisonous to host animals. For example, during infections by certain gram-negative bacteria such as *E. coli,* a lipopolysaccharide (LPS) is released from the cell wall as it is broken down. The LPS can then induce the death of cells in the host animal. Toxemic conditions occur in animals in which toxins such as LPS are made available, i.e., in septic conditions, or conditions of systemic disease caused by the multiplication of microorganisms in the circulation (see, e.g., Stedman's Medical Dictionary (Illustrated), supra at pages 1274–1275 and 1464). Toxemia can also result from exposure of the animal to traumatic stimuli, e.g., physical or chemical trauma.

However, as sepsis/trauma syndrome is not limited in causation to infections, it is possible that no endotoxin is involved, but nonetheless, the release of factors such as TNF, IL-1 complement and leukotrienes is triggered.

"Auto-immune disorders," such as systemic lupus erythematosus, juvenile diabetes, multiple sclerosis and Hashimoto's thyroiditis, are characterized by an animal's immune system attacking its own tissues.

Treatment of these, and other disorders, is accomplished according to the method of this invention by administering to the affected animal an amount of the multilamellar liposome of this invention which comprises an anti-disorder effective amount of the arachidonic acid metabolite. "Anti-disorder effective" amounts of an arachidonic acid metabolite are any amounts effective to ameliorate, inhibit or prevent the cell activation and adhesion, inflammation, toxemia, or other indication associated with the disorder being treated. Typically, the effective amount of the metabolite comprises at least about $10^{-12}$ g of the metabolite per kg of body weight of the animal, and desirably, from about $10^{-12}$ g per kg to about $10^{-3}$ g/kg. More desirably, the effective amount of the metabolite comprises from about $10^{-8}$ g per kg of body weight to about $10^{-4}$ g per kg. Most desirably, the effective amount comprises about $10^{-6}$ g of the arachidonic acid metabolite per kg of body weight of the animal.

Cells which become activated and subsequently undergo intracellular adhesion can also have surface receptors for arachidonic acid metabolites. Without intending to be limited by theory, it is believed that binding of arachidonic acid metabolites to these receptors can reduce activation and adhesion-associated damage by deactivating the cell surface receptors responsible for the elevated levels of intercellular adhesion. $PGE_1$, for example, has been shown to be a potent inhibitor of both neutrophil and platelet aggregation, as well as the binding of these cells to activated vascular endothelial cells. Without cell-cell binding, cofactors such as $O_2^-$ and various degradative enzymes cannot be released, and tissue damage is eliminated. Deactivation is believed to be induced by a protein kinase A-mediated increase in intracellular cAMP levels instigated by the metabolite/receptor interaction.

Arachidonic acid metabolites such as $PGE_1$ are also believed to have the ability to both prevent inflammation, and to turn it off once it has been initiated. It has been found that the extracellular release by neutrophils of mediators of inflammation can be modulated by the elevation or depletion of intracellular stores of cyclic adenosine monophosphate (cAMP) and cyclic guanosine monophosphate (cGMP). Elevation of cAMP reduces release of mediators of inflammation whereas increases in the levels of cGMP enhances the excretion of those mediators. cAMP is sometimes referred to as the "universal off-switch" since increasing intracellular levels of cAMP can turn off inflammation, regardless of the factor that initially turned it on.

Generally, liposomal arachidonic acid metabolite formulations offer significant advantages for therapeutic administration, for example, lower dosage to achieve the desired effect and reduced side effects, in comparison to administration of the free forms of the metabolites. Free, i.e., non-liposomal, $PGE_1$ and $PGI_2$, for example, have been found (see, Jugdutt et al., "Dissimilacts of Prostacycn, Prostaglandin E Prostaglandin Myocardial Infarct ze after Coronarusion in Conscious," Circulation CH, 49(3) :685–700 981) to have scant effect in reducing the infarct size in dogs which were reperfused after simulation of a myocardial infarction by placement of an occluder snare around a coronary artery. In the reported tests, the prostaglandin was administered via continuous arterial infusion over a six-hour period, resulting in the administration of a relatively large dose of the drug.

Continuous infusion is believed to be required because of the short in vivo half-lives of free prostaglandins, due to their rapid inactivation in the lungs. Furthermore, the distribution of high levels of $PGE_1$ in vivo is known to induce systemic effects such as hypotension, tachycardia and diarrhea. Such side effects generally limit the amount of free metabolites which can be effectively administered.

Use of the liposomal formulations of this invention increases the circulatory half-lives of administered arachidonic acid metabolites, with generally reduced side effects.

Furthermore, liposomes can be particularly advantageous vehicles for delivering prostaglandins to their intended sites of action. Without being bound by a particular theory or mechanism, it is believed that the liposomes are attracted to the activated cells and adhere to the activated surfaces. The prostaglandin is then readily available at the site of injury to deliver its anticellular adhesion action. One theory for the attraction of liposomes to adhesion activated cells is that liposomes are opsonized by fibronectin and vitronectin in the blood. Opsonization is the process by which bacteria are altered such that they become more readily and efficiently engulfed by phagocytes. Thus opsonized liposomes would be more readily attracted to the activated neutrophils which express receptors for fibronectin and vitronectin, thereby delivering the associated prostaglandin to the affected sites.

Liposomal arachidonic acid metabolite formulations in which the metabolite is associated with the liposome by way of a pH gradient across the liposome's lipid bilayer can be therapeutically useful. Liposomal formulations having an internal acidic aqueous buffer, such as a citric acid buffer, particularly a pH 4.5 citric acid buffer, are preferred for establishing transbilayer pH gradients. Arachidonic acid metabolites associated with liposomes by such gradients tend to remain associated with the liposome as long as the pH gradient is maintained. However, when the gradient decays in the bodies of animals to which the liposome has been administered, and the internal pH consequently increases, arachidonic acid metabolites generally become unassociated with the liposome. The metabolite then is more likely, than when it is associated with a liposome, to be able to interact with the corresponding surface receptors on cells, such as neutrophils, that become activated and that subsequently undergo intercellular adhesion.

"Anti-disorder effective" amounts of an arachidonic acid metabolite are any amounts effective to ameliorate, inhibit or prevent the cell activation and adhesion, inflammation, toxemia, or other indication associated with the disorder being treated according to the method of this invention. Typically, the effective amount of the metabolite comprises at least about $10^{-12}$ g of the metabolite per kg of body weight of the animal, and desirably, from about $10^{-12}$ g per kg to about $10^{-3}$ g/kg. More desirably, the effective amount of the metabolite comprises from about $10^{-8}$ g per kg of body weight to about $10^{-4}$ g per kg. Most desirably, the effective amount comprises about $10^{-6}$ g of the arachidonic acid metabolite per kg of body weight of the animal.

The method of this invention can comprise administering a bioactive agent, for example, an antimicrobial or anti-inflammatory agent, to the animal in addition to the arachidonic acid metabolite administered. The additional bioactive agent can also be an additional arachidonic acid metabolite.

This invention is further described in the following Examples. However, those of ordinary skill in the art will readily determine that these examples are merely illustrative of the invention as defined in the claims which follow thereafter.

EXAMPLES

Example 1
Preparation of Multilamellar Liposomes (MLVs) Containing $PGE_1$
Preparation of EPC-Containing $PGE_1$ MLVs An egg phosphatidylcholine (EPC) stock solution (20 mg/ml in ethanol) was prepared as follows: 1 g of dried EPC was dissolved in 50 ml of absolute ethanol, with gentle swirling, in a 50-ml brown bottle with a Teflon-lined lid. The resulting solution was stored at minus 20 degrees Celsius. A $PGE_1$ stock solution (1 mg/ml in ethanol) was prepared as follows: 20 mg of dried $PGE_1$ was transferred to a 20-ml vial, to which 20 ml of absolute ethanol was added. The $PGE_1$ was dissolved in the ethanol with gentle swirling; the resulting solution was stored at minus 20 degrees Celsius.

An aliquot of the EPC stock solution (9.75 ml), and an aliquot of the $PGE_1$ stock solution (0.5 ml), were combined in a 500-ml round-bottom flask; the ethanol was removed by rotoevaporation at about 30 degrees C. for at least two hours. The dried $EPC/PGE_1$ was resuspended in a pH 4.5 buffer (e.g., 50 mM acetate, 150 mM NaCl, pH brought to 4.5 with 10N NaOH; glass beads aided in resuspension of the dried $EPC/PGE_1$) so as to form a liposome suspension. This suspension was stored at 4 degrees C.

Preparation of DPPC-Containing $PGE_1$ MLVs

A DPPC stock solution was prepared as described above, using 1.035 g of dipalmitoyl phosphatidylcholine (DPPC) dissolved in methylene chloride. Rehydration of the dried $DPPC/PGE_1$ mixture required heating in a water bath, with swirling, at about 52 degrees C. for about 3–5 minutes.

TABLE 1

$PGE_1$ FORMULATIONS

| Lipid | % Bound and/ or Entrapped at | |
|---|---|---|
| | pH 4.6 | pH 7.1 |
| EPC | 90 | 54 (60)* |
| | 90 | 61 (68) |
| | 89 | 56 (63) |
| DPPC | 60 | 42 (68) |
| | 59 | 38 (64) |
| | 53 | 35 (67) |

*The numbers in parentheses represent the percentage of prostaglandin bound and/or entrapped at pH 4.6 which remains in the pellet at pH 7.1.

The data (see Table 1, above, and Table 2, below) show that about 90% of the available prostaglandin was associated with EPC multilamellar vesicles when a prostaglandin-containing citrate buffer, pH 4.6 was used to rehydrate dried lipids so as to form liposomes. When these same liposomes were transferred to a pH 7.1 buffer, about 54–61% of the available prostaglandin remained associated with the liposomes after one half hour. When DPPC was used to make the multilamellar vesicles, about 53–60% of the available prostaglandin was entrapped in liposomes comprising the pH 4.6 buffer. When these liposomes were transferred to the pH 7.1 buffer, about 35–42% of the available prostaglandin remained within the liposomes after one half hour.

TABLE 2

$PGE_1$ FORMULATIONS

| Lipid | % Bound and/ or Entrapped at pH 7.12 | |
|---|---|---|
| | 0.5 Hours | 4.5 Hours |
| EPC | 54 (60) | 31 (35)* |
| | 61 (68) | 35 (39) |
| | 56 (63) | 31 (35) |
| DPPC | 42 (68) | 31 (51) |
| | 38 (64) | 26 (44) |
| | 35 (67) | 25 (47) |

*The numbers in parentheses represent the percentage of prostaglandin bound and/or entrapped at pH 4.6 which remains in the pellet at pH 7.1.

Example 2
Rat Air Pouch Studies

The rat subcutaneous air pouch, a model for acute inflammation and leukocyte extravasation from the peripheral vasculature to sites of inflammation (Tate, et al., Laboratory Investigation 59:192 (1988), the contents of which are incorporated herein by reference), was used to study the effect of systemic $PGE_1$ liposomes in mediating fMLP induced fMLP inflammation.

Male Sprague-Dawley rats, weighing 126–150 g, were obtained from Charles River Laboratories. Upon receipt, the rats were acclimated in the animal facility for 2 days. Throughout the experiments, the rats were watered and fed ad libitum. For air pouch formation, the rats were anesthetized via inhalent, their backs shaved, and swabbed with ethyl alcohol. Twenty cc of ambient air was injected subcutaneously into the animal's back to form an air pouch, and the animal was returned to it's cage. The air pouches were monitored to determine integrity, and additional air was injected, if warranted. At six days following air pouch formation, intra-air pouch inflammation was induced by direct injection into the air pouch of 2.15 μg fMLP. Free prostaglandin $E_1$, or $PGE_1$ liposome formulations, were simultaneously injected i.v. via the tail vein, and the animals returned to their cages. Six hours after stimulation, the rats were sacrificed by $CO_2$ inhalation, and the total exudate fluid recovered from the air pouch via syringe. The results of these experiments are presented in FIGS. 2–6.

Visual examination of the post-stimulation air pouch lining indicated that fMLP effected a thickening of the lining and a large number of invasive leukocytes, as compared to control animals, in which saline alone was injected into the air pouch. Treatment with free $PGE_1$ resulted in a reduction in vascular reactivity and a concurrent reduction in the number of leukocytes invading the pouch lining. The neutrophil population evident in the lining was transient, i.e., the leukocytes were in the process of extravasation from the vasculature to the lumen/exudate fluid of the air pouch. Since the leukocytes were transiently crossing the air pouch lining, the subsequent analysis of liposomal prostaglandin formulations in ameliorating leukocyte invasion was confined to those cells present in the aspirated exudate fluid.

Experiments were performed to evaluate the effect of $PGE_1$ liposomes in mediating cellular influx to the air pouch. These experiments compared C-53 (unilamellar liposomal $PGE_1$) and MLV-$PGE_1$ (multilamellar liposomal $PGE_1$) with free $PGE_1$. The free stable prostaglandin analog 15-methyl-$PGE_1$ was included in these experiments due to its longer bioavailability of $\geq 8$ hours, as compared to the <15 min. bioavailability of free $PGE_1$.

Figure 1:
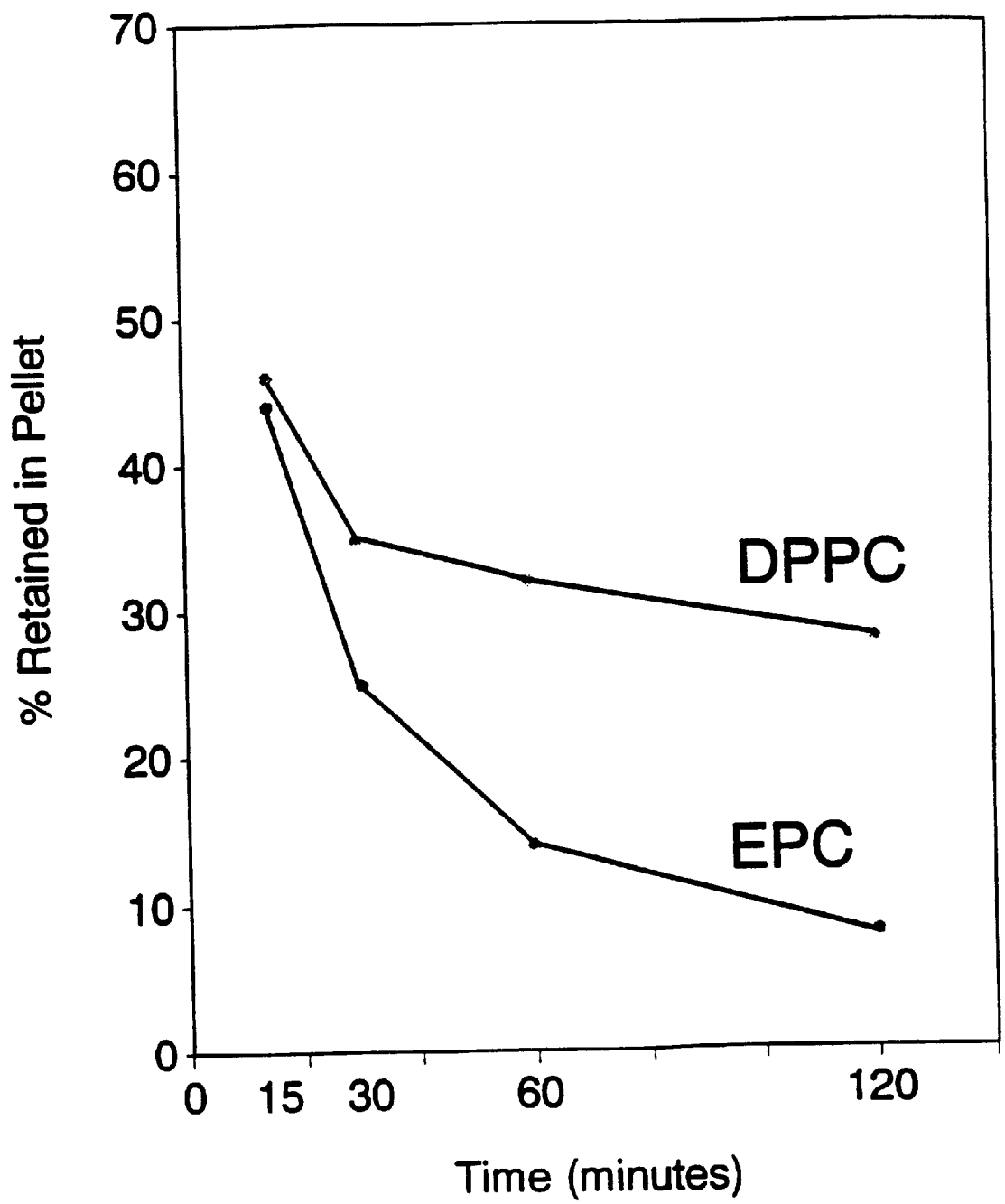
FIG. 1. Release of $PGE_1$ from MLVs. The release of prostaglandin $E_1$ ($PGE_1$) from multilamellar vesicles (MLVs) comprising egg phosphatidylcholine (EPC) or dipalmitoyl phosphatidylcholine (DPPC) formed in 50 mM citrate buffer, pH 4.5, and then incubated at room temperature in pH 7.1 buffer for the indicated amount of time, is set forth. X-axis: time (minutes); y-axis: percent $PGE_1$ retained in pelleted liposomes.
Figure 2:
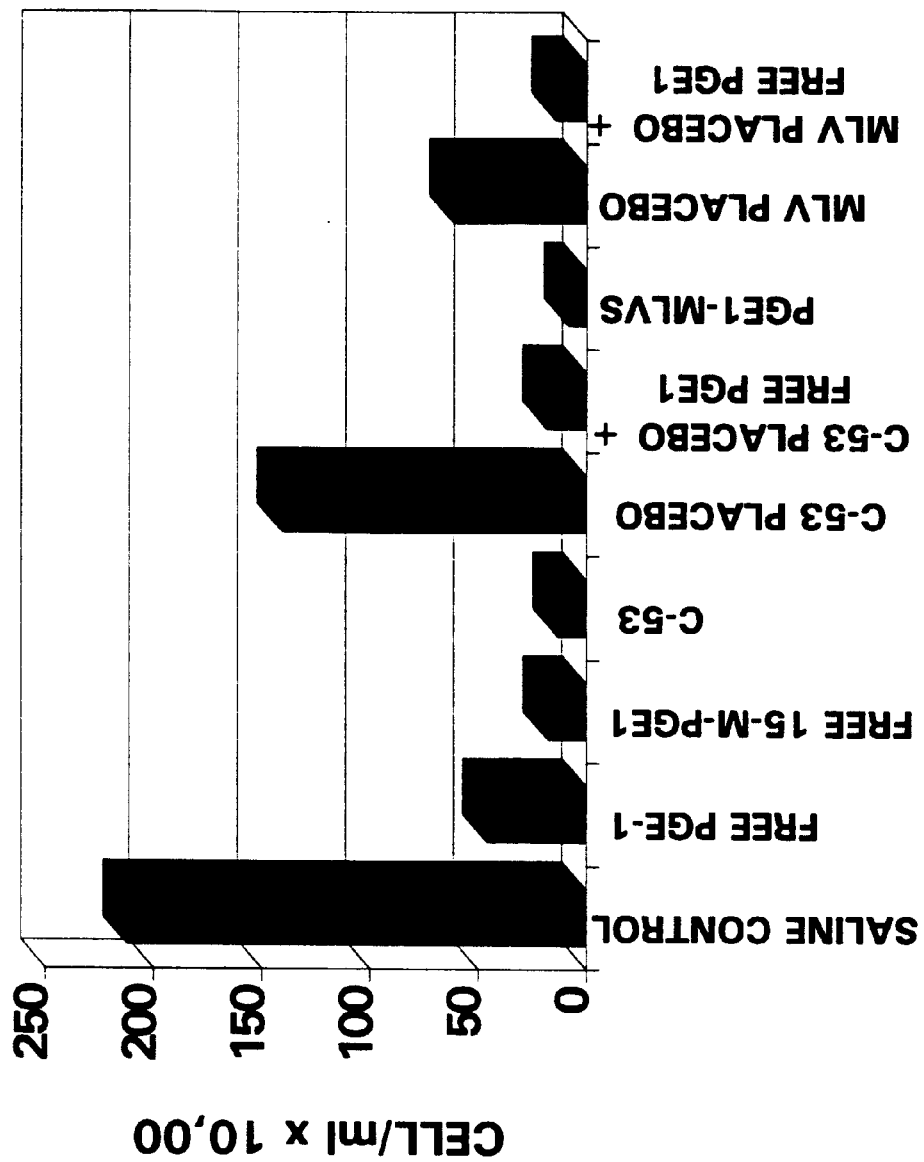
FIG. 2. Rat Air Pouch Studies. Liposomal $PGE_1$ formulations inhibit the extravasation of leukocytes from the vasculature to the rat air pouch. Subcutaneous air pouches were formed in male Sprague-Dawley rats. fMLP (2.15 μg) was injected directly into the air pouch at time 0, and free or liposomal $PGE_1$ was simultaneously injected intravenously. After six hours, the air pouch exudate was collected and the air pouch total cell population determined. For each treatment group, n=4. X-axis: saline control, free $PGE_1$, free 15-M-$PGE_1$ (15-methyl-$PGE_1$), C-53 $PGE_1$ formulation (unilamellar liposomal $PGE_1$), C-53 placebo (liposomes without $PGE_1$), C-53 placebo liposomes plus free $PGE_1$, $PGE_1$-MLVs (multilamellar liposomes), MLV placebo liposomes, MLV placebo liposomes plus free $PGE_1$; y-axis: cells/ml×10,000 in exudate.

As shown in FIG. 2, both C-53 and MLV-$PGE_1$ inhibited the influx of cells to the air pouch more effectively than free $PGE_1$. MLV-$PGE_1$ was more inhibitory than C-53. Both C-53, and MLV, placebo liposomes inhibited the cellular extravasation in the absence of $PGE_1$; when this placebo inhibition was increased with the addition of free $PGE_1$ to the placebos.

Figure 3:
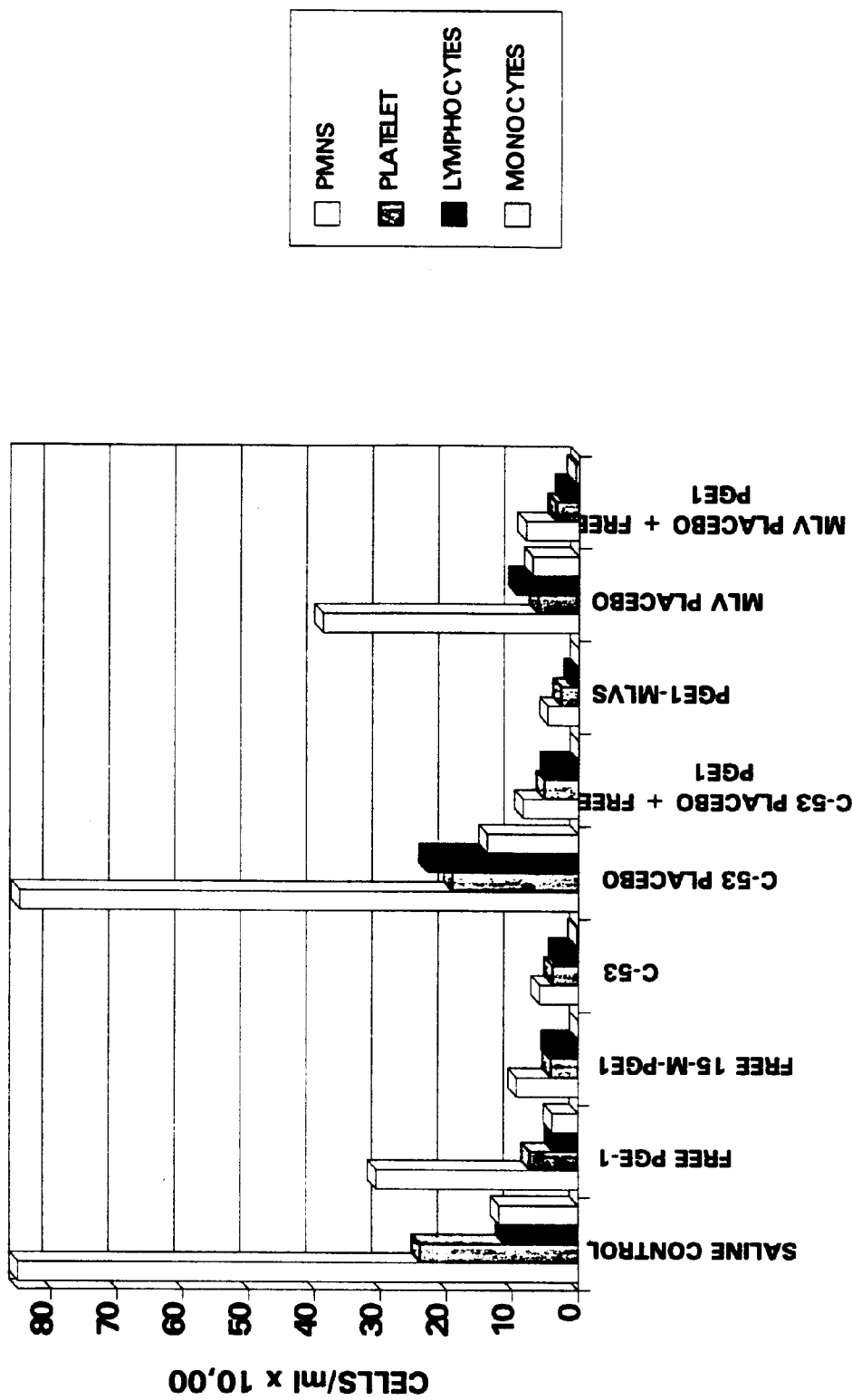
FIG. 3. Inhibition of Leukocyte Subset Extravasation. Subcutaneous air pouches were formed in male Sprague-Dawley rats. fMLP (2.15 μg) was injected directly into the air pouch at time 0, and free or liposomal $PGE_1$ was simultaneously injected intravenously. After six hours, the air pouch exudate was collected, and the air pouch total cell population determined. The figure is scaled for prostaglandins. The value for neutrophils in the saline control was off the scale used, and was 1.62×10⁶ neutrophils/ml. For each treatment group, n=4. First column in each set (unshaded): polymorphonucleocytes (PMNS); second column (lightly shaded): platelets; third column (darkly shaded): lymphocytes; fourth column (unshaded): monocytes. Y-axis: cells/ml×10,000 in exudate.

The leukocyte subset distribution in the air pouch exudate was also determined and this data is shown in FIG. 3, below. All leukocyte subpopulations were preferentially inhibited by $PGE_1$ liposome formulations as compared to free $PGE_1$. The predominate leukocyte subpopulation extravasating into the air pouch in response to fMLP is neutrophils. The greatest inhibition was seen for this neutrophil population. Monocyte influx to the air pouch was completely abolished by liposomal $PGE_1$, but not by free $PGE_1$.

Figure 4:
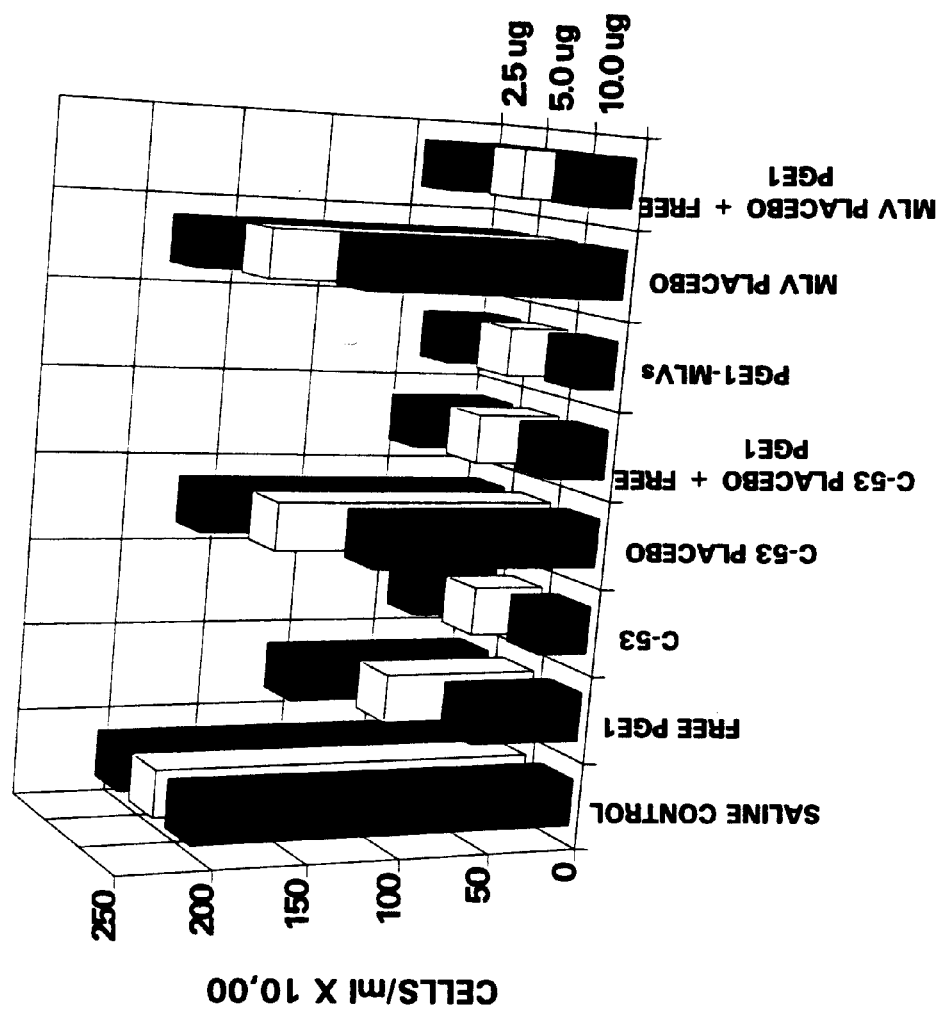
FIG. 4. Dose Response of Inhibition of Leukocyte Extravasation. Subcutaneous air pouches were formed in male Sprague-Dawley rats. fMLP (2.15 μg) was injected directly into the air pouch at time 0, and free or liposomal $PGE_1$ was simultaneously injected intravenously. After six hours, the air pouch exudate was collected, and the air pouch total cell population determined. The figure is scaled for prostaglandins. The value for neutrophils in the saline control was off the scale used, and was 1.62×10⁶ neutrophils/ml. For each treatment group, n=4. X-axis: saline control, free $PGE_1$, C-53, C-53 placebo liposomes, C-53 placebo liposomes plus free $PGE_1$, $PGE_1$-MLVs, MLV placebo liposomes, MLV placebo liposomes plus free $PGE_1$; y-axis: cells/ml×10,000 in exudate. Darkly shaded columns: 25

The dose responses of inhibition of leukocytes extravasation in response to free $PGE_1$ and liposomal $PGE_1$ are shown in FIG. 4. As shown, the inhibition of leukocyte influx to the rat air pouch is dose-dependently inhibited by $PGE_1$ liposomes. Maximal inhibition is attained at 10.0 μg/kg, as greater concentrations have no additional effect. Leukocyte subpopulation was similar to that shown in FIG. 3, as all leukocyte subpopulations were preferentially inhibited by $PGE_1$ liposome formulations, as compared to free $PGE_1$. The greatest inhibition was seen for the neutrophil population, and the monocyte influx to the air pouch was completely abolished by liposomal $PGE_1$, but not by free $PGE_1$. The above data indicated that $PGE_1$-MLVs had a slightly greater inhibitory response on air pouch extravasation that C-53. To further separate the response to these two formulations, we assessed the air pouch leukocyte population at both 6 and 24 hours. This data is shown in FIG. 5, below.

The leukocyte subpopulation distribution in these experiments was similar to that shown in FIGS. 3 and 4, as: a) the predominate leukocyte population infiltrating the air pouch was comprised of neutrophils; and b) all leukocyte subpopulations were preferentially inhibited by $PGE_1$ liposome formulations as compared to free $PGE_1$. Monocytes were absent at 6 hours, but present in small numbers at 24 hours (>$4\times10^4$ in all treatment groups as compared to $7.8\times10^4$ for the 24 hour saline control).

The efficacy of alternative $PGE_1$ liposome formulations in mediating leukocyte extravasation to the rat air pouch was assessed. The specific formulations assessed, along with their characteristics, are listed below in Table 3 (see below), with the data from these experiments being presented in FIG. 6.

TABLE 3

Alternative $PGE_1$ Liposome Formulations

| Formulation | Characteristics |
|---|---|
| EPC SPLV | Multi-lamellar, and similar to MLVS as to $PGE_1$ leak rate. |
| EPC/Chol/POPE-GA/$PGE_1$ | Surface modified with glutaric acid to effect circulation times of up to 24 hours. $PGE_1$ is membrane associated. |
| EPC/Chol/POPE-GA | Surface modified with glutaric acid to effect circulation times of up to 24 hours. No $PGE_1$. |
| EPC/Chol/POPE-GA/DOPE-$PGE_1$ | Surface modified with glutaric acid to effect circulation times of up to 24 hours. $PGE_1$ covalently linked to the membrane. |
| EPC/Chol/DOPE-$PGE_1$ | $PGE_1$ is membrane associated. |

As these data indicate, all $PGE_1$ liposome formulations are more efficacious than free $PGE_1$ in inhibiting leukocyte extravasation to the rat air pouch. The leukocyte subpopulation distribution in these experiments was similar to that shown in FIGS. 4 and 5, as: a) the predominate leukocyte population infiltrating the air pouch was comprised of neutrophils, and b) all leukocyte subpopulations were preferentially inhibited by $PGE_1$ liposome formulations as compared to free $PGE_1$. Monocytes were absent in all liposomal $PGE_1$ treatment groups.

Example 3

Adjuvant Arthritis

Male Lewis rats, weighing 126–150 g each, were obtained from Charles River Laboratories. Upon receipt, the rats were acclimated in the animal facility for 2 days. Throughout the experiments the rats were watered and fed ad libitum. Chronic bilateral arthritis was induced by the i.d. (intradural) injection of complete Freund's adjuvant at the base of the tail. The onset of arthritis was abrupt, occurring between days 10 and 14 in Freund's induced animals. The symptoms exhibited by untreated control animals were tenderness upon palpation in most active joints, symmetric edema involving the joints of the paws, ankles and knees, flexation contractures of the forepaws, malaise, and weight loss attributable to both primary disease as well as inability or disinclination to access food supplies, due to pain and decreased mobility.

Experiments were conducted to assess the efficacy of free $PGE_1$ in mediating the progression of adjuvant arthritis. The parameters assessed in these experiments were changes in joint size measured at the rear knee, changes in body weight, and a subjective scoring of general health, vigor and motility. The results from these experiments are shown in FIGS. 7–12.

The data in FIGS. 7, 8 and 9 indicates that free $PGE_1$ attenuated the progression of adjuvant arthritis, as objectively determined by maintaining weight gain and inhibiting joint edema. Subjective scoring indicated a maintenance of general health and mobility in $PGE_1$-treated animals. The rats could be treated as late as 10 days post-adjuvant administration and still receive protection from disease progression, although the inhibition of arthritis progression was not as profound as that seen in animals treated with $PGE_1$ beginning at day 0.

Because of the protective effect of free $PGE_1$ in ameliorating arthritis, we next addressed the question of whether liposomal $PGE_1$ was as effective as free $PGE_1$. The experiments included the same objective parameters and subjective scoring as in the previous experiments, and compared C-53, $PGE_1 30$ containing MLVs and free $PGE_1$. The data from these experiments are shown in FIGS. 10, 11 and 12, and indicate a greater efficacy for liposomal than free $PGE_1$ in decreasing the progression of rat adjuvant induced arthritis.

The optimal formulation thus far tested is $PGE_1$-containing MLVs, presumably because of longer bioavailability of $PGE_1$ due to slower leak rate. MLV formulations effected an almost total inhibition of disease manifestation and progression.

Example 4

Rat Endotoxemia

Fever, hypotension, changes in leukocyte counts and diarrhea are symptoms of gram-negative bacterial infections. These infections may lead to disseminated intravascular coagulation and irreversible shock. A large volume of literature indicates the involvement of leukocyte derived IL-1, IL-6 and TNFα in mediating the progression of endotoxic shock. Because our in vitro data indicated an inhibition of these cytokines from cultured monocytes, we developed an in vivo model of rat endotoxemia, using mortality as an end point, to assess the effectiveness of $PGE_1$ liposome formulations in attenuating LPS-induced death.

Experiments were designed to establish an $LD_{50}$ for *E. coli* LPS (lipopolysaccharide) in Sprague-Dawley rats. The data from these experiments are shown in FIG. 13, and indicate that the $LD_{50}$ is at 50 μg/kg. This LPS dosage was used in subsequent experiments, unless otherwise indicated.

Experiments was designed to assess the efficacy of free and liposomal $PGE_1$ in mediating LPS-induced mortality. The results from these experiments is shown in FIG. 14, and indicate that free $PGE_1$ increased both the rate and magnitude of LPS induced mortality. In contrast, C-53 afforded almost complete protection against LPS induced death. $PGE_1$-containing MLVs imparted also protection. All animals receiving LPS exhibited non purulent conjunctivitis, profuse watery diarrhea and profound lethargy. These symptoms were manifested within the first two hours post-LPS administration, and persisted throughout the time course of the experiment. Dying animals exhibited syncope and shock.

What is claimed is:

1. A method of treating an animal afflicted with a cell activation and adhesion, inflammation or toxemic disorder which comprises administering to the animal a composition comprising a pharmaceutically acceptable carrier and a multilamellar liposome comprising: (i) a prostaglandin; (ii) multiple bilayers comprising an amphipathic phospholipid; and, (iii) multiple aqueous compartments comprising a release-inhibiting citric acid buffer, wherein the phospholipid consists essentially of a phospholipid having saturated acyl chains and wherein an anti-disorder effective amount of the prostaglandin comprising from about $10^{-12}$ g to about $10^{-3}$ g of the prostaglandin per kg of the animal's body weight is administered per dose of the composition.

2. The method of claim 1, wherein the administration comprises intravenous administration.

3. The method of claim 1, wherein the animal is a human.

4. The method of claim 1, wherein the liposome comprises a solute entrapped in its aqueous compartments and wherein the concentration of the solute in each of the aqueous compartments of the liposome is substantially equal.

5. The method of claim 1, wherein the prostaglandin is prostaglandin E1.

6. The method of claim 1, wherein the buffer is a citric acid buffer having a pH of about 4.5.

7. The method of claim 1, wherein the disorder comprises reperfusion injury, systemic inflammatory response syndrome, myocardial infarction, adult respiratory distress syndrome, vasculitis, burn injury, post-traumatic shock, a vaso-occlusive disorder, an arthritic disorder or an autoimmune disorder.

8. The method of claim 7, wherein the arthritic disorder is rheumatoid arthritis, gout or filary arthritis.

9. The method of claim 7, wherein the autoimmune disorder is systemic lupus erythematosus, juvenile diabetes, multiple sclerosis or Hashimoto's thyroiditis.

10. The method of claim 7, wherein the disorder comprises systemic inflammatory response syndrome.

11. The method of claim 7, wherein the disorder comprises adult respiratory distress syndrome.

12. The method of claim 1, wherein the effective amount of the prostaglandin is from about $10^{-8}$ g of the prostaglandin per kg of body weight of the animal to about $10^{-4}$ g per kg of body weight.

13. The method of claim 12, wherein the effective amount of the prostaglandin is about $10^{-6}$ g of the prostaglandin per kg of body weight of the animal.

14. The method of claim 7, comprising administering an additional bioactive agent to the animal.

15. The method of claim 14, wherein the additional bioactive agent is an antimicrobial, anti-inflammatory or vasodilative agent.

16. The method of claim 14, wherein the additional bioactive agent is an additional prostaglandin.

17. The method of claim 1, herein the liposome comprises a drying protectant at both the inside and outside surfaces of its bilayers.

18. The method of claim 17, wherein the drying protectant is a sugar selected from the group consisting of glucose, sucrose, maltose, lactose, galactose, trehalose, or raffinose.

19. The method of claim 1, wherein the liposome has been dehydrated, stored and then rehydrated prior to administration to the animal.

* * * * *